(12) United States Patent
Murata et al.

(10) Patent No.: US 8,691,857 B2
(45) Date of Patent: Apr. 8, 2014

(54) EP4 AGONIST

(71) Applicants: Asahi Glass Company, Limited, Tokyo (JP); Kaken Pharmaceutical Co., Ltd., Tokyo (JP)

(72) Inventors: Takahiko Murata, Tokyo (JP); Masahiro Amakawa, Kyoto (JP); Shin Teradaira, Kyoto (JP); Yasushi Matsumura, Tokyo (JP); Katsuhiko Konishi, Tokyo (JP)

(73) Assignees: Asahi Glass Company, Ltd., Tokyo (JP); Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/675,530

(22) Filed: Nov. 13, 2012

(65) Prior Publication Data

US 2013/0072530 A1    Mar. 21, 2013

Related U.S. Application Data

(63) Continuation of application No. 12/917,935, filed on Nov. 2, 2010, now Pat. No. 8,394,844, which is a continuation-in-part of application No. PCT/JP2009/065690, filed on Sep. 8, 2009.

(30) Foreign Application Priority Data

Sep. 10, 2008 (JP) ................... 2008-232133
Jul. 16, 2009 (JP) ................... 2009-168193

(51) Int. Cl.
*C07D 405/06* (2006.01)
*A61K 31/4025* (2006.01)

(52) U.S. Cl.
CPC .......... *C07D 405/06* (2013.01); *A61K 31/4025* (2013.01)
USPC .......................................... 514/382; 548/252

(58) Field of Classification Search
USPC ............ 514/381, 469; 548/250; 549/305, 465
See application file for complete search history.

(56) References Cited

U.S. PATENT DOCUMENTS

| | | | |
|---|---|---|---|
| 5,538,995 | A | 7/1996 | Matsumura et al. |
| 5,616,732 | A | 4/1997 | Matsumura et al. |
| 5,747,531 | A | 5/1998 | Matsumura et al. |
| 5,972,965 | A | 10/1999 | Taniguchi et al. |
| 6,127,413 | A | 10/2000 | Kurumatani et al. |
| 6,248,766 | B1 | 6/2001 | Ohkawa et al. |
| 6,300,344 | B1 | 10/2001 | Taniguchi et al. |
| 6,335,038 | B1 | 1/2002 | Cavazza |
| 6,340,693 | B1 | 1/2002 | Kurumatani et al. |
| 6,417,213 | B2 | 7/2002 | Ohkawa et al. |
| 6,555,559 | B1 | 4/2003 | Wakita et al. |
| 7,402,605 | B2 | 7/2008 | Tani et al. |
| 2002/0006944 | A1 | 1/2002 | Ohkawa et al. |
| 2011/0098481 | A1* | 4/2011 | Murata et al. ............ 548/252 |

FOREIGN PATENT DOCUMENTS

| | | | |
|---|---|---|---|
| DE | 2405255 | A | 8/1974 |
| EP | 1 988 087 | A1 | 11/2008 |
| JP | 02-500371 | A | 2/1990 |
| JP | 07-324081 | A | 12/1995 |
| JP | 07-330752 | A | 12/1995 |
| JP | 10-194992 | A | 7/1998 |
| JP | 2004-256547 | A | 9/2004 |
| WO | WO 89/00563 | A1 | 1/1989 |
| WO | WO 97/03973 | A1 | 2/1997 |

(Continued)

OTHER PUBLICATIONS

Abramovitz et al., *Biochimica et Biophysica Acta*, 1483: 285-293 (2000).
Angulo et al., *Br. J. Pharmacol.*, 136: 23-30 (2002).
Arakawa et al., *Japanese J. Clin. Med.*, 42(1): 89-94 (1984).
Chang et al., *Prostaglandins*, 53: 83-90 (1997).
Fabricius et al., *J. Immunology*, 184: 677-684 (2010).
Foudi et al., *British Journal of Pharmacology*, 154: 1631-1639 (2008).
Graham et al., *Expert Opin. Investig. Drugs.*, 18(6): 749-766 (2009).

(Continued)

*Primary Examiner* — Michael Barker
(74) *Attorney, Agent, or Firm* — Leydig, Voit & Mayer, Ltd.

(57) ABSTRACT

Provided is a compound represented by the formula (1):

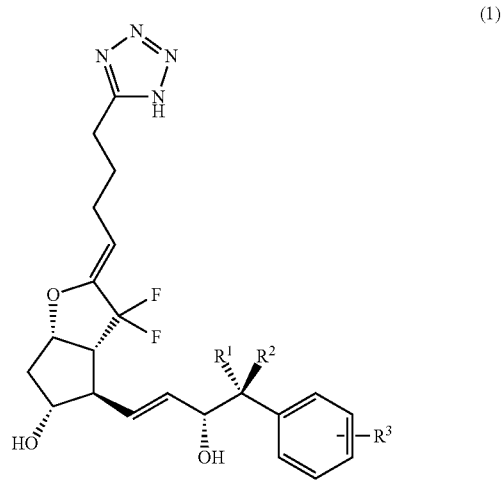

wherein $R^1$ and $R^2$ are each independently a hydrogen atom or a straight chain alkyl group having a carbon number of 1-3, $R^3$ is a hydrogen atom, an alkyl group having a carbon number of 1-4, an alkoxyalkyl group, an aryl group, a halogen atom or a haloalkyl group, or a pharmaceutically acceptable salt thereof, which has, unlike known $PGI_2$ analogs, a selective EP4 agonist action, and a medicament containing the compound, which is useful for the prophylaxis and/or treatment of immune diseases, diseases of the digestive tract, cardiovascular diseases, cardiac diseases, respiratory diseases, neurological diseases, ophthalmic diseases, renal diseases, hepatic diseases, bone diseases, skin diseases and the like.

5 Claims, 26 Drawing Sheets

(56) References Cited

FOREIGN PATENT DOCUMENTS

| WO | WO 97/17974 A1 | 5/1997 |
|---|---|---|
| WO | WO 98/13356 A1 | 4/1998 |
| WO | WO 98/41209 A1 | 9/1998 |
| WO | WO 99/66913 A2 | 12/1999 |
| WO | WO 00/24727 A1 | 5/2000 |
| WO | WO 03/103664 A1 | 12/2003 |
| WO | WO 2008/116670 A1 | 10/2008 |
| WO | WO 2010/029925 A1 | 3/2010 |

OTHER PUBLICATIONS

Grigsby et al., *Biology of Reproduction*, 75: 297-305 (2006).
Hishikari et al., *Cardiovascular Research*, 81: 123-132 (2009).
Hori et al., *Neuroscience*, 160: 813-819 (2009).
Hristovska et al., *Hypertension*, 50: 525-530 (2007).
Jiang et al., *The Journal of Pharmacology and Experimental Therapeutics*, 320(1): 22-28 (2007).
Jiang et al., *World Journal of Gastroenterology*, 15(41): 5149-5156 (2009).
Jones et al., *British Journal of Pharmacology*, 134: 313-324 (2001).
Kabashima et al., *The Journal of Clinical Investigation*, 109(7): 883-893 (2002).
Kiriyama et al., *British Journal of Pharmacology*, 122: 217-224 (1997).
Konturek et al., *Prostaglandins*, 28(4): 443-453 (1984).
Kuzumoto et al., *Transplant Proceedings*, 37: 422-424 (2005).
Lai et al., *Am. J. Respir. Crit. Care Med.*, 178: 188-196 (2008).
Li et al., *Neuroscience Letters*, 438: 210-215 (2008).
Minami et al., *Journal of Biological Chemistry*, 283(15): 9692-9703 (2008).
Nitta et al., *Scand. J. Immunol.*, 56: 66-75 (2002).
Patani et al., *Chem Rev.*, 96(8): 3147-3176 (1996).
Prasanna et al., *Exp. Eye Res.*, 89: 608-617 (2009).
Sakai et al., *Kobe J. Med. Sci.*, 47: 35-45 (2001).
Schaaf et al., *J. Med. Chem.*, 22 (11): 1340-1346 (1979).
Sekiguchi et al., *Spine*, 31(8): 869-872 (2006).
Shi et al., *J. Immunology*, 184: 7207-7218 (2010).
Torii et al., *Biochem. Biophys. Res. Commun.*, 290: 696-700 (2002).
Vukicevic et al., *Kidney Int.*, 70: 1099-1106 (2006).
Wermuth, ed., *Saishin Soyaku Kagaku*, $1^{st}$ edition, vol. 1, pp. 235-271 (Technomics, Inc., 2008).
Wermuth, ed., *The Practice of Medicinal Chemistry*, $1^{st}$ edition, part III, chapter 13, pp. 203-237 (Academic Press, 1996).
Yoshida et al., *Proc. Natl. Acad. Sci. USA.*, 99(7): 4580-4585 (2002).
Zushi et al., *Therapeutic Res.*, 18(Supp. 1): 138-143 (1997).
Japanese Patent Office, International Search Report in International Patent Application No. PCT/JP2011/055411 (Apr. 26, 2011).
Japanese Patent Office, International Search Report in International Patent Application No. PCT/JP2009/065690 (Oct. 13, 2009).
Echeverria et al., *European Journal of Neuroscience*, 22: 2199-2206 (2005).
Figiel, *Acta Neurobiol. Exp.*, 68: 526-534 (2008).
Ikeda-Matsuo et al., *Journal of Neuroimmunology*, 238: 34-43 (2011).
Lee et al., *Journal of Neuroimmunology*, 155: 21-31 (2004).
Liang et al., *The Journal of Clinical Investigation*, 121(11): 4362-4371 (2011).
Mei-Ling et al., *Neuroscience Letters*, 508: 31-36 (2012).
Milatovic et al., *NeuroToxicology*, 32: 312-319 (2011).
Miyagishi et al., *Journal of Pharmacological Sciences*, 121: 347-350 (2013).
Sugimoto et al., *The Journal of Biological Chemistry*, 282: 11613-11617 (2007).
Zhen et al., *Neurobiology of Aging*, 33: 2215-2219 (2012).

\* cited by examiner

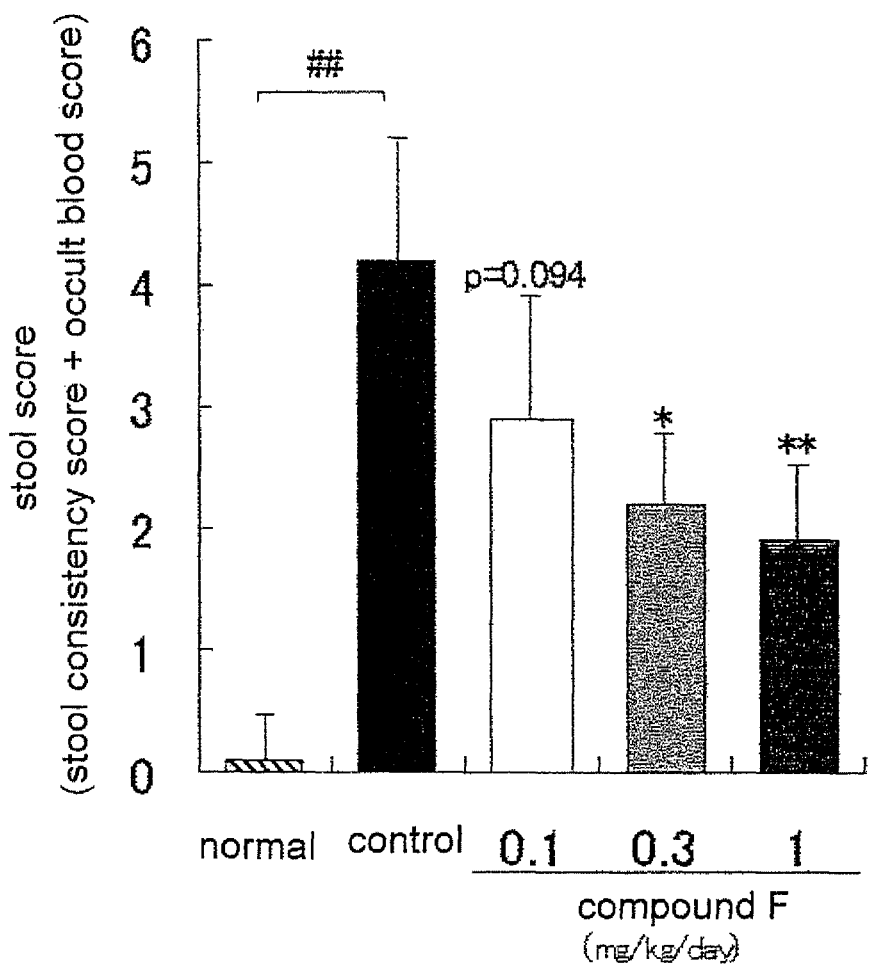

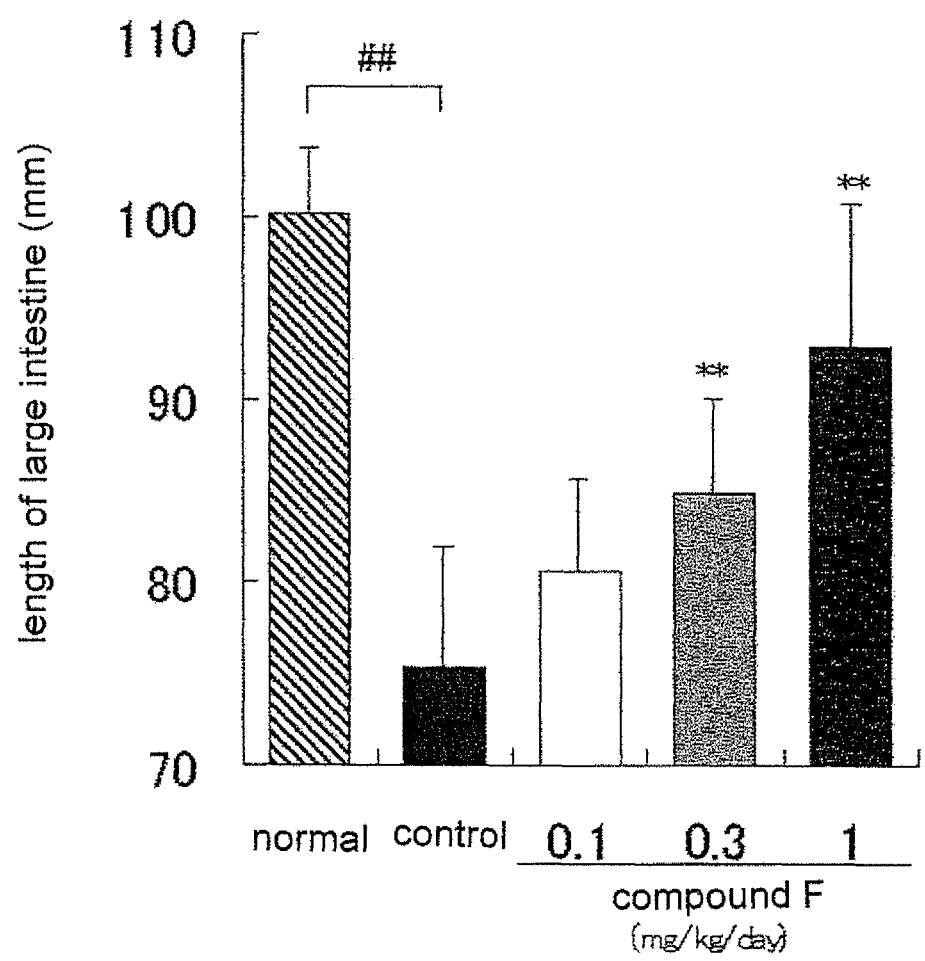

** p<0.01 versus control p<0.01 p<0.01
** p<0.01 versus control

\## p<0.01
** p<0.01 versus control

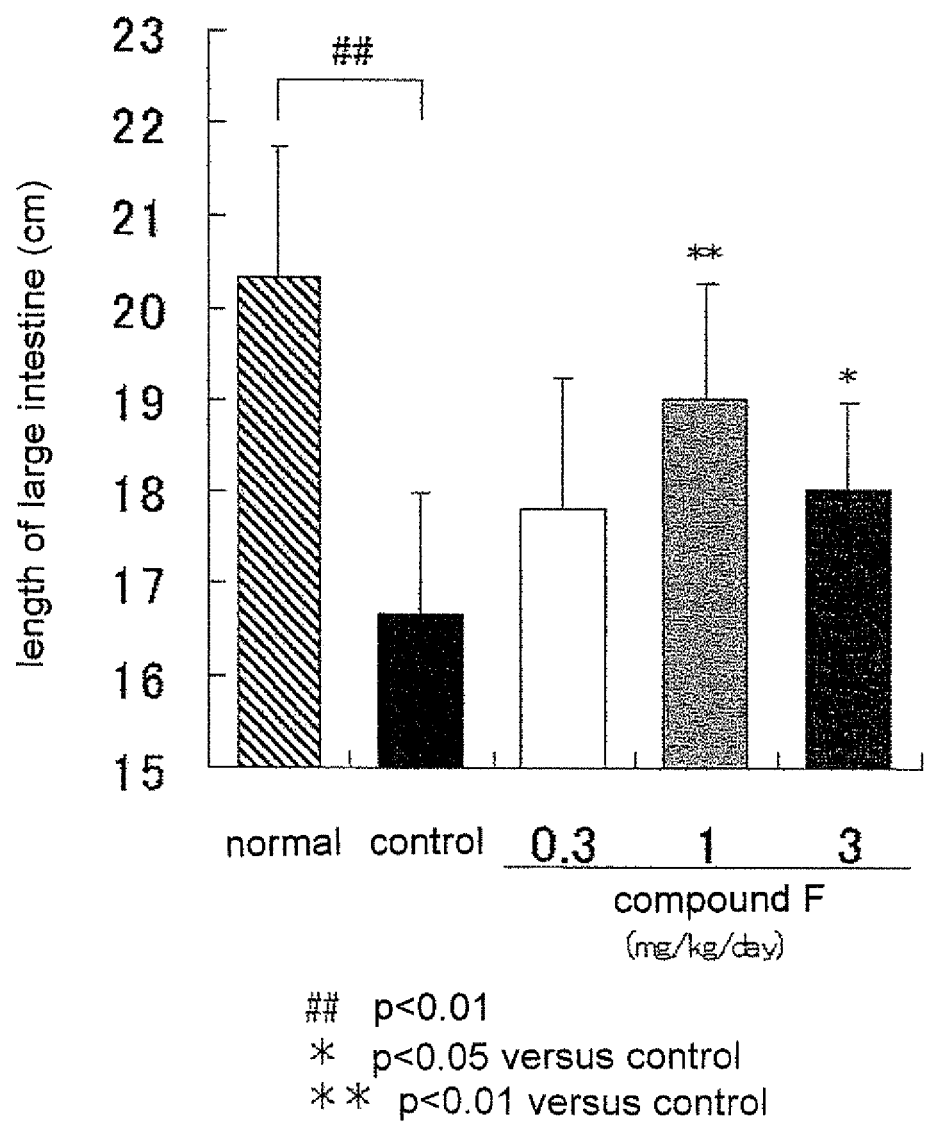

* p<0.05 versus control

** p<0.01 versus control

** p<0.01 versus control

\* p<0.05 versus control p<0.01 p<0.01
** p<0.01 versus control p<0.01
** p<0.01 versus control

\# p<0.05
\* p<0.05 versus control

*, ** p<0.05, p<0.01 versus solvent control, respectively

**     $p<0.01$ versus control

EP4 AGONIST

CROSS-REFERENCE TO RELATED APPLICATIONS

This patent application is a continuation of copending U.S. patent application Ser. No. 12/917,935, filed Nov. 2, 2010, which is a continuation-in-part of International Patent Application PCT/JP2009/065690, filed Sep. 8, 2009, and which claims priority to Japanese Patent Application 2009-168193, filed Jul. 16, 2009, and Japanese Patent Application 2008-232133, filed Sep. 10, 2008, the contents of which are encompassed in their entireties herein.

TECHNICAL FIELD OF THE INVENTION

The present invention relates to a 7,7-difluoroprostaglandin $I_2$ derivative wherein the carboxy group at C-1 of prostaglandin (hereinafter to be referred to as PG) is substituted by a tetrazole group, and two fluorine atoms are bonded at C-7 of PG, or a pharmaceutically acceptable salt thereof, a pharmaceutical composition thereof, and a pharmaceutical use thereof. More specifically, the present invention relates to a 7,7-difluoroprostaglandin $I_2$ derivative which is an EP4 agonist useful for the prophylaxis or treatment of immune diseases, cardiovascular diseases, cardiac diseases, respiratory diseases, ophthalmic diseases, renal diseases, hepatic diseases, bone diseases, diseases of the digestive tract, neurological diseases, skin diseases and the like.

BACKGROUND OF THE INVENTION

Natural PGs each bind to their specific receptors, and exhibit characteristic actions. A receptor for each of $PGI_2$, $PGE_2$, $PGD_2$, $PGF_2\alpha$ and thromboxane $A_2$ ($TXA_2$) is called IP, EP, DP, FP and TP, respectively. Furthermore, EP further has four subtypes, EP1, EP2, EP3 and EP4. These PG receptors show different expression patterns in the organs and cells, and even if the receptors are expressed in the same cell, the actions shown thereby are different.

While the derivatives of the natural PGs are under influence of the original carbon skeleton, they come to bind to various receptors as the structures change (non-patent documents 1 and 2).

PG derivatives having a tetrazole group instead of the carboxy group at C-1 of prostaglandin have been reported in the following patent documents 1-4, non-patent document 2 and the like. Furthermore, 7,7-difluoro $PGI_2$ analogs and manufacturing methods thereof have been reported (patent documents 5 and 6). In addition, 7,7-difluoro $PGI_2$ analogs are described to be useful as prophylactic or therapeutic agents for cardiovascular diseases (patent document 5). 7,7-Difluoro $PGI_2$ analogs not only bind to IP strongly, but also bind to EP1-4 weakly (non-patent documents 4 and 5). However, a selective EP4 agonist, which is one of the 7,7-difluoro $PGI_2$ analogs, shows weak binding affinity to IP, EP1, EP2 and EP3 and strongly and selectively binds only to EP4, has not been reported.

EP4 is expressed in the immune cells, inflammatory cells, digestive organs, blood vessels, neuronal cells, eyes, kidney, bone and the like, and EP4 agonists are researched and developed as a medicament of immune diseases, diseases of the digestive tract, cardiovascular diseases, cardiac diseases, neurological diseases, ophthalmic diseases, renal diseases, hepatic diseases, bone diseases and the like.

The EP4 agonists inhibit TNF-α production, promote IL-10 production, suppress inflammation and immunoreaction, and are considered to be useful for the prophylaxis and/or treatment of immune diseases or inflammatory diseases such as autoimmune diseases (e.g., amyotrophic lateral sclerosis, multiple sclerosis, Sjogren's syndrome, rheumatoid arthritis, systemic lupus erythematosus), post-transplantation rejection and the like, asthma, neuronal cell death, arthritis, lung injury, pulmonary fibrosis, emphysema, bronchitis, chronic obstructive pulmonary disease, hepatopathy, acute hepatitis, nephritis (acute nephritis, chronic nephritis), renal failure, systemic inflammation response syndrome, sepsis, hemophagocytic syndrome, macrophage activation syndrome, Still's disease, Kawasaki disease, burn, systemic granuloma, ulcerative colitis, Crohn's disease, hypercytokinemia at dialysis, multiple organ failure, shock and psoriasis.

EP4 agonists are considered to be useful for the prophylaxis and/or treatment of arteriosclerosis since they suppress activation of macrophages (non-patent document 6).

EP4 agonists are considered to be useful as an agent for the prophylaxis and/or treatment of angina pectoris or myocardial infarction, since they have a protective action against cardiac ischemia-reperfusion injury (non-patent document 7).

EP4 agonists are considered to be also useful as an agent for the prophylaxis and/or treatment of a brain disorder induced by cerebral hemorrhage, cerebral infarction, subarachnoid hemorrhage and the like, since they have a protective action against ischemia-reperfusion injury in the brain as well (non-patent document 8).

EP4 agonists are considered to be also useful as an agent for the prophylaxis and/or treatment of an ischemia-reperfusion injury in the liver (non-patent document 9).

EP4 agonists are considered to be useful as an agent for the prophylaxis and/or treatment of glaucoma, since they have an intraocular pressure-lowering action (non-patent document 10).

EP4 agonists are considered to be also useful for the prophylaxis and/or treatment of glomerulonephritis and diabetic nephritis, since EP4 is abundantly expressed in the renal glomerulus (non-patent document 11).

EP4 agonists are considered to be also useful for the prophylaxis and/or treatment of calvities, alopecia and the like, since EP4 is also involved in hair growth and hair restoration (non-patent document 12).

EP4 agonists are considered to be useful as a (promoting) agent of cervical ripening, since EP4 is also involved in cervical ripening (non-patent document 13).

EP4 agonists are considered to be useful as an agent for the prophylaxis and/or treatment of osteoporosis, or as a healing promoter of bone fracture, since EP4 is also involved in an osteogenic action (non-patent documents 14 and 15).

Since EP4 is expressed in blood vessels and EP4 agonists relax blood vessels and contribute to increased blood flow, it is considered to be useful for the prophylaxis and/or treatment of pulmonary arterial hypertension, peripheral arterial obstruction (arteriosclerosis obliterans and thromboangiitis obliterans) and various symptoms (intermittent claudication with lumbar spinal stenosis, leg numbness, Raynaud's syndrome, erectile dysfunction, hemorrhoids etc.) attributed to peripheral circulatory disturbance (non-patent documents 16-20).

EP4 is expressed in fibroblasts, and an EP4 agonist is considered to promote expression of basic fibroblast growth factor and is useful for promotion of healing of pressure ulcer and wound (non-patent document 21).

It has been reported that EP4 is expressed in the cochlea, and an EP4 agonist is also useful for the prophylaxis and/or treatment of hearing disorder caused by sound (non-patent document 22).

Inflammation of the digestive tract is observed in the mouth cavity, esophagus, stomach, small intestine, large intestine and anus, and includes acute inflammation and chronic inflammation. When the mucosal epithelia are affected by physical or chemical stimuli, or are infected by bacteria or virus, inflammation is induced, and erosions or ulcerous lesions occur depending on the level of the inflammation. Excessive secretion of gastric acid due to a stress causes gastritis, gastric ulcer or duodenal ulcer. In addition, excessive ingestion of alcohol induces congestion of mucosal blood flow or reflux of gastric acid due to reduced stomach motility, thus causing gastritis, gastric ulcer, duodenal ulcer or esophagitis. Orthopedic patients, rheumatoid arthritis patients and the like under a long term administration of a non-steroidal anti-inflammatory drug suffer from drug-induced gastric ulcer or duodenal ulcer. In addition, cancer patients develop radiation enteritis with radiation therapy or drug-induced enteritis with anti-cancer drug treatment. Furthermore, patients infected with tuberculosis, amebic dysentery and the like develop infectious enterogastritis such as intestinal tuberculosis and amebic colitis. Besides these, ischemic enteritis and the like are developed by ischemia due to blood flow obstruction. If immunity of patients with inflammation of digestive tract is abnormal, even when the cause is removed, repair of the organ is prevented and conditions become chronic. Of these inflammatory diseases of the digestive tract, the diseases with inflammation in the intestine are referred to as inflammatory bowel disease in a broad sense.

On the other hand, there are inflammatory intestinal diseases of unidentified cause. Ulcerative colitis and Crohn's disease are two well known diseases, which are inflammatory bowel disease in a narrow sense. Furthermore, it also includes similar diseases such as intestinal Behcet's disease and simple ulcer. They are intractable chronic gastrointestinal diseases along with repeated remission and relapse, where main etiology of the disease is considered to be less protection of the intestinal epithelium, or abnormal intestinal immune response against enteric bacteria entering into the intestinal tissues.

Ulcerative colitis is a chronic colon disease in which erosions and ulcers are formed in the large intestinal mucosa continuously from the rectum, and symptoms thereof include abdominal pain, diarrhea, bloody stool, fever and the like. On the other hand, in Crohn's disease, a lesion can occur in any digestive tract from the mouth cavity to large intestine and anus. This disease is characterized by discontinuous longitudinal ulcer and cobblestone-like appearance in the gastrointestinal tract, and the symptoms thereof include abdominal pain, diarrhea, fever, undernutrition due to malabsorption of nutrients, anemia, and the like.

For the prophylaxis and/or treatment of inflammation in inflammatory diseases of the digestive tract, in case of with a known cause, the cause is removed or suppressed. For example, antacid, anticholinergic agent, histamine H2 receptor antagonist, proton pump inhibitor and the like are used against inflammation in gastritis, gastric ulcer, duodenal ulcer and the like to suppress secretion and actions of gastric acid. In other instances, PGE derivatives and the like are used to supplement $PGE_2$ for inflammation induced by a non-steroidal anti-inflammatory drug, which inhibits $PGE_2$ production. However, $PGI_2$ derivatives are not used.

On the other hand, the prophylaxis or treatment of inflammatory bowel disease in a narrow sense includes drug therapy, nutrition (diet) therapy and surgical therapy. For the drug therapy, 5-aminosalicylic acid preparations (pentasa, salazopyrin), steroids (prednisolone), immunosuppressants (azathiopurine, mercaptopurine and tacrolimus), anti-TNF-α antibodies (infliximab) and the like are used. It has been recently reported that an EP4 agonist is effective for inflammatory bowel disease (non-patent documents 23-25).

In addition, since EP4 is also involved in mucosal-protective action, an EP4 agonist is considered to be useful for the prophylaxis and/or treatment of gastrointestinal tract injury such as gastric ulcer, duodenal ulcer and the like, and stomatitis (non-patent document 26).

PRIOR ART DOCUMENTS

Patent Documents patent document 1: DE 2405255
patent document 2: WO 03/103664
patent document 3: WO 00/24727
patent document 4: U.S. Pat. No. 7,402,605
patent document 5: JP-A-7-330752
patent document 6: JP-A-2004-256547

Non-Patent Documents non-patent document 1: Biochim. Biophys. Acta, 1483: 285-293 (2000).
non-patent document 2: Br. J. Pharmacol., 122: 217-224 (1997).
non-patent document 3: J. Med. Chem., 22: 1340-1346 (1979).
non-patent document 4: Prostaglandins, 53: 83-90 (1997).
non-patent document 5: Br. J. Pharmacol., 134: 313-324 (2001).
non-patent document 6: J. Biol. Chem., 283: 9692-9703 (2008).
non-patent document 7: Cardiovasc. Res., 81: 123-132 (2009).
non-patent document 8: Neurosci. Lett., 438: 210-215 (2008).
non-patent document 9: Transplant. Proc., 37: 422-424 (2005).
non-patent document 10: Exp. Eye Res., 89: 608-617 (2009).
non-patent document 11: Kidney Int., 70: 1099-1106 (2006).
non-patent document 12: Biochem. Biophys. Res. Commun., 290: 696-700 (2002).
non-patent document 13: Biol. Reprod., 75: 297-305 (2006).
non-patent document 14: Proc. Natl. Acad. Sci. USA., 99: 4580-4585 (2002).
non-patent document 15: Expert Opin. Investig Drugs., 18: 746-766 (2009).
non-patent document 16: Hypertension, 50: 525-530 (2007).
non-patent document 17: Br. J. Pharmacol., 154: 1631-1639 (2008)
non-patent document 18: Am. J. Respir. Crit. Care Med., 178: 188-196 (2008).
non-patent document 19: Spine, 31: 869-872 (2006),
non-patent document 20: Br. J. Pharmacol., 136: 23-30 (2002)
non-patent document 21: Kobe J. Med. Sci., 47: 35-45 (2001).
non-patent document 22: Neuroscience, 160: 813-819 (2009).
non-patent document 23: J. Clin Invest., 109: 883-893 (2002).
non-patent document 24: Scand. J. Immunol., 56: 66-75 (2002).
non-patent document 25: J. Pharmacol. Exp. Ther., 320: 22-28 (2007).
non-patent document 26: World J. Gastroenterol., 15: 5149-5156 (2009).

SUMMARY OF THE INVENTION

Problems to be Solved by the Invention

The present invention aims to provide a compound which is a novel prostaglandin $I_2$ derivative, superior in metabolic stability, and selectively binds to a specific prostaglandin receptor.

Means of Solving the Problems

In an attempt to solve the aforementioned problems, the present inventors have synthesized novel PG analogs conferred with particular properties of fluorine atom and conducted studies to clarify the property and physiological activity thereof. As a result, the inventors have found that a novel 7,7-difluoro $PGI_2$ derivative, wherein the carboxy group at 0-1 of the prostanoic acid skeleton is substituted by a tetrazole group and two fluorine atoms are bonded, is excellent in the property and pharmacological action, that unexpectedly, even though it is a $PGI_2$ derivative, it has a selective EP4 agonist activity and considerably loses an IP agonist activity, which is observed in the carboxylate form at C-1, and that it is an excellent chemical as a medicament due to such agonist actions, which resulted in the completion of the present invention. The selective EP4 agonist can be an active ingredient of a medicament with reduced side effects via other receptors.

As far as the present inventors know, synthetic examples, property, physiological activity and the like of $PGI_2$ analogs, wherein the C-1 of PG is a tetrazole group and two fluorine atoms are present at the C-7 of PG, have not been published at all.

Therefore, the present invention provides a 7,7-difluoro $PGI_2$ derivative represented by the following formula (1), which is a selective EP4 agonist (hereinafter sometimes to be abbreviated as compound (1) of the present invention), a pharmaceutically acceptable salt thereof, and a medicament containing the same as an active ingredient, and relates to the following.

[1] A compound represented by the formula (1):

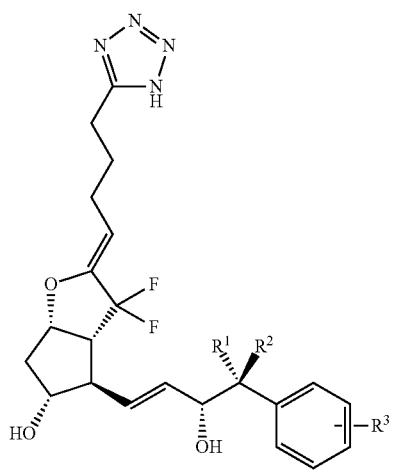

(1)

wherein $R^1$ and $R^2$ are each independently a hydrogen atom or a straight chain alkyl group having a carbon number of 1 to 3, and $R^3$ is a hydrogen atom, an alkyl group having a carbon number of 1 to 4, an alkoxyalkyl group, an aryl group, a halogen atom or a haloalkyl group), or a pharmaceutically acceptable salt thereof.

[2] The compound of [1], wherein $R^1$ is a methyl group, or a pharmaceutically acceptable salt thereof.
[3] The compound of [1] or [2], wherein $R^3$ is a methyl group, or a pharmaceutically acceptable salt thereof.
[4] The compound of any of [1] to [3], wherein $R^2$ is a hydrogen atom, or a pharmaceutically acceptable salt thereof.
[5] The compound of any of [1] to [4], wherein $R^1$ is a methyl group, and $R^2$ is a hydrogen atom, or a pharmaceutically acceptable salt thereof.
[6] The compound of any of [1]-[5], wherein $R^3$ is an m-methyl group, or a pharmaceutically acceptable salt thereof.
[7] The compound of [1], wherein $R^1$ is a methyl group, $R^2$ is a hydrogen atom, and $R^3$ is a methyl group, or a pharmaceutically acceptable salt thereof.
[8] The compound of [1], wherein $R^1$ is a hydrogen atom, $R^2$ is a methyl group, and $R^3$ is a methyl group, or a pharmaceutically acceptable salt thereof.
[9] 4-[(Z)-(1S,5R,6R,7R)-6-[(1E,3R,4RS)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane, or a pharmaceutically acceptable salt thereof.
[10] 4-[(Z)-(1S,5R,6R,7R)-6-[(1E,3R,4R)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane, or a pharmaceutically acceptable salt thereof.
[11] 4-[(Z)-(1S,5R,6R,7R)-6-[(1E,3R,4S)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane, or a pharmaceutically acceptable salt thereof.
[12] A medicament comprising the compound of any of [1] to [11], or a pharmaceutically acceptable salt thereof as an active ingredient.
[13] A medicament for the prophylaxis or treatment of a disease of the digestive tract, comprising the compound of any of [1] to [11], or a pharmaceutically acceptable salt thereof as an active ingredient.
[14] The medicament of [13], wherein the disease of the digestive tract is an inflammatory disease or ulcerative disease of the digestive tract.
[15] The medicament of [14], wherein the inflammatory disease of the digestive tract is an inflammatory bowel disease.
[16] The medicament of [15], wherein the inflammatory bowel disease is ulcerative colitis or Crohn's disease.
[17] The medicament of [15], wherein the inflammatory bowel disease is intestinal Behcet's disease or simple ulcer.
[18] The medicament of [14], wherein the ulcerative disease of the digestive tract is esophagitis, esophageal ulcer, gastritis or gastric ulcer.
[19] The medicament of [18], wherein the gastritis or gastric ulcer is drug-induced gastritis or gastric ulcer.
[20] The medicament of [19], wherein the drug-induced gastritis or gastric ulcer is induced by a non-steroidal anti-inflammatory drug.
[21] The medicament of [18], wherein the gastritis or gastric ulcer is induced by alcohol.
[22] The medicament of [14], wherein the ulcerative disease of the digestive tract is small intestinal ulcer.
[23] The medicament of [22], wherein the small intestinal ulcer is drug-induced small intestinal ulcer.
[24] The medicament of [23], wherein the drug-induced small intestinal ulcer is induced by a non-steroidal anti-inflammatory drug.
[25] The medicament of [22], wherein the small intestinal ulcer is induced by alcohol.
[26] An EP4 agonist comprising the compound of any of [1] to [11], or a pharmaceutically acceptable salt thereof.

[27] A medicament comprising the EP4 agonist of [26] as an active ingredient.
[28] The medicament of [27] for the prophylaxis or treatment of a disease involving EP4.
[29] The medicament of [28] for the prophylaxis or treatment of a disease whose symptoms can be mitigated by a selective EP4 agonist action.
[30] The medicament of [29], wherein the disease whose symptoms can be mitigated by a selective EP4 agonist action is an immune disease, a cardiovascular disease, a cardiac disease, a respiratory disease, an ophthalmic disease, a renal disease, a hepatic disease, a bone disease, a disease of the digestive tract, a neurological disease or a skin disease.
[31] The medicament of [30], wherein the immune disease is amyotrophic lateral sclerosis, multiple sclerosis, Sjogren's syndrome, rheumatoid arthritis, systemic lupus erythematosus, post-transplantation rejection, arthritis, systemic inflammation response syndrome, sepsis, hemophagocytic syndrome, macrophage activation syndrome, Still's disease, Kawasaki disease, hypercytokinemia at dialysis, multiple organ failure, shock or psoriasis.
[32] The medicament of [30], wherein the cardiovascular disease or cardiac disease is arteriosclerosis, angina pectoris, myocardial infarction, brain disorder caused by cerebral hemorrhage, brain disorder caused by cerebral infarction, brain disorder caused by subarachnoid hemorrhage, pulmonary arterial hypertension, peripheral arterial obstruction (arteriosclerosis obliterans and thromboangiitis obliterans) or various symptoms attributed to peripheral circulatory disturbance (intermittent claudication or leg numbness caused by lumbar spinal stenosis, Raynaud's syndrome, erectile dysfunction, hemorrhoids etc.).
[33] The medicament of [30], wherein the respiratory disease is asthma, lung injury, pulmonary fibrosis, emphysema, bronchitis or chronic obstructive pulmonary disease.
[34] The medicament of [30], wherein the ophthalmic disease is glaucoma or ocular hypertension.
[35] The medicament of [30], wherein the renal disease is glomerulonephritis, diabetic nephropathy, IgA nephropathy or renal ischemia-reperfusion injury.
[36] The medicament of [30], wherein the hepatic disease is hepatitis, hepatopathy or hepatic ischemia-reperfusion injury.
[37] The medicament of [30], wherein the bone disease is osteoporosis, bone fracture or a postoperative recovery phase after osteotomy.
[38] The medicament of [30], wherein the neurological disease is neuronal cell death.
[39] The medicament of [30], wherein the skin disease is pressure ulcer or wound.
[40] The medicament of [28], wherein the disease involving EP4 is a disease selected from the group consisting of calvities, alopecia, cervical ripening failure and a hearing disorder.

Effect of the Invention

The novel 7,7-difluoro $PGI_2$ derivative afforded by the present invention can provide a medicament which maintains blood concentration for a long time and exhibits a pharmacological action by parenteral administration or oral administration, and which is for the prophylaxis or treatment of inflammation of the digestive tract or the onset of diarrhea or blood feces in inflammatory bowel disease, or for the prophylaxis or treatment of gastritis or ulcer in gastric ulcer, small intestinal ulcer and the like. Furthermore, due to the EP4 agonist action, a medicament for the prophylaxis or treatment of immune diseases, cardiovascular diseases, cardiac diseases, respiratory diseases, ophthalmic diseases, renal diseases, hepatic diseases, bone diseases, diseases of the digestive tract, neurological diseases, skin diseases and the like can be provided. In clinical situations, the compound of the present invention is expected to show similar efficacy in the disease group for which an EP4 agonist can provide effects, whereas the concern of side effects such as hemorrhage, hypotension, palpitation and face flush is lower because of its weaken IP agonist action on the circulatory system. Particularly, the compound of the present invention is effective, based on the EP4 agonist action, for inflammation of the digestive tract associated with immunity, drug-induced mucosal injury of the digestive tract, injury of the digestive tract and delayed healing due to mucosal regenerative disorder, ophthalmic diseases, renal diseases, and hepatic diseases.

Specifically, the compound is useful for inflammatory bowel disease such as ulcerative colitis and Crohn's disease, alcoholic gastritis, gastric ulcer and small intestinal ulcer, nephritis, glaucoma, ocular hypertension, hepatitis and the like.

BRIEF DESCRIPTION OF THE DRAWINGS

FIG. 2A shows the effect on abnormal stool in mouse (BALB/c) DSS colitis model.
FIG. 2B shows the effect on colon shortening in mouse (BALB/c) DSS colitis model.
FIG. 4B shows the effect on colon shortening in rat DSS colitis model.

EMBODIMENT OF THE INVENTION

Definition

Figure 1A:
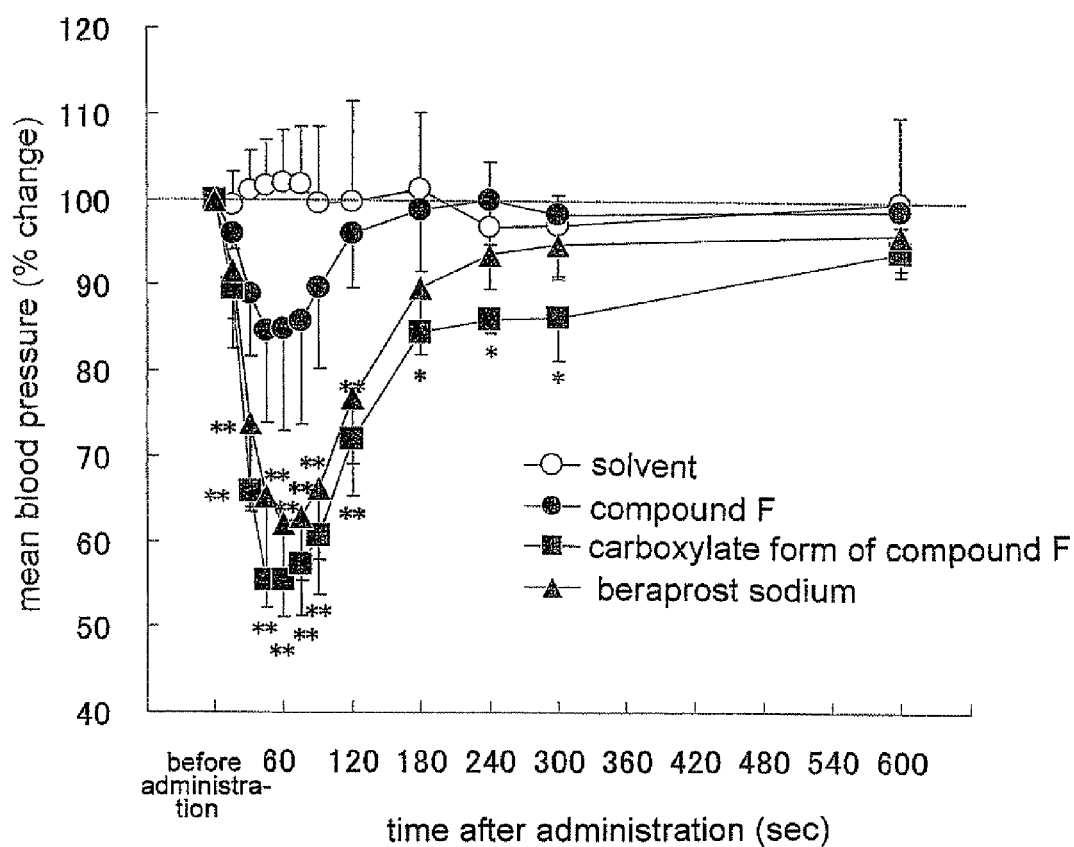
FIG. 1A shows the effect on blood pressure in mice.

In the present specification, the "selective EP4 agonist" means a compound which shows a weak agonist action (pharmacological activity) on $PGI_2$ receptor (IP) relative to the agonist action generally found in $PGI_2$ analogs, and has a remarkably superior agonist action on $PGE_2$ receptor subtype EP4 as compared to IP agonist action. The EP4 agonist action can be measured in accordance with the measurement method of the agonist activity described in the below-mentioned Example 19. The IP agonist action can be measured in accordance with the method described in Example 20. Whether a compound is a selective EP4 agonist can be evaluated by measuring the ratio of binding inhibition constant Ki values of EP4 and IP (IP/EP4% ratio) in the same species in accordance with the measurement method described in Example 18. Examples of the selective EP4 agonist include a compound having the aforementioned ratio of not less than 5, preferably not less than 10, more preferably not less than 50, most preferably not less than 100.

In the present specification, the "prostaglandin $I_2$ derivative" means a compound with a structure modified by a general technique in the organic chemistry, based on the structure of natural type $PGI_2$. In the following, the compound of the present invention is explained.

Definition of the Compound of the Present Invention

In the nomenclature of the compounds in the present specification, the numbers used to show the position in PG skeleton correspond to the numbers in the prostanoic acid skeleton. In the present specification, a group in which a hydrogen atom of an alkyl group is substituted is also indicated as a substituted alkyl group. The same applies to other groups.

In addition, a "lower" organic group such as alkyl group and the like means that the carbon number thereof is 1 to 6. The carbon number of the "lower" organic group is preferably 1 to 4.

The "alkyl group" may be a straight chain or a branched chain. Unless otherwise specified, the alkyl group is preferably a lower alkyl group having a carbon number of 1 to 6, and a lower alkyl group having a carbon number of 1 to 4 is particularly preferable. Examples of the alkyl group include a methyl group, an ethyl group, a propyl group, an isopropyl group, a butyl group, an isobutyl group, a sec-butyl group, a tert-butyl group, a pentyl group, a hexyl group and the like.

The "alkoxy group" is preferably a lower alkoxy group having a carbon number of 1 to 6, particularly preferably an alkoxy group having a carbon number of 1 to 4. The alkoxy group may be a straight chain or a branched chain. Examples of the alkoxy group include a methoxy group, an ethoxy group, a propoxy group, a butoxy group and the like.

The "alkoxyalkyl group" is an alkyl group substituted by an alkoxy group. The alkoxy group of the alkoxyalkyl group is preferably a lower alkoxy group having a carbon number of 1 to 4, and the alkyl group of the alkoxyalkyl group is preferably a lower alkyl group having a carbon number of 1 to 4. The alkoxyalkyl group is preferably a lower alkoxyalkyl group (that is, the carbon number of the whole alkoxyalkyl group is 1 to 6), more preferably a lower alkoxyalkyl group having a carbon number of 1 to 4. Examples of the alkoxyalkyl group include a methoxymethyl group, an ethoxymethyl group, a propoxymethyl group, an ethoxyethyl group and the like.

The "aryl group" is a monovalent aromatic hydrocarbon group optionally having substituent(s). As an aryl group without a substituent, a phenyl group is preferable.

As the "substituted aryl group" (an aryl group having substituent(s)), an aryl group wherein one or more hydrogen atoms in the aryl group are substituted by a lower alkyl group, a halogen atom, a halogenated (lower alkyl) group, a lower alkoxy group and the like is preferable. Preferable examples of the substituted aryl group include a substituted phenyl group, and particular examples thereof include a monohalophenyl group (e.g., chlorophenyl group, fluorophenyl group, bromophenyl group etc.), a (halogenated lower alkyl) substituted phenyl group (e.g., trifluoromethylphenyl group etc.) and a (lower alkoxy)phenyl group (e.g., methoxyphenyl group, ethoxyphenyl group etc.).

The "halogen atom" is a fluorine atom, a chlorine atom, a bromine atom or an iodine atom.

The "haloalkyl group" is an alkyl group wherein one or more hydrogen atoms in the alkyl group are substituted by a halogen atom, and preferred is a lower haloalkyl group having a carbon number of 1 to 6. Examples of the haloalkyl group include a fluoromethyl group, a difluoromethyl group, a trifluoromethyl group, a trifluoroethyl group, a pentafluoroethyl group, a chloromethyl group, a bromomethyl group and the like.

As compound (1) of the present invention, the following compound is preferable from the aspects of pharmacological activity and physical property.

That is, $R^1$ and $R^2$ are each independently a hydrogen atom or a straight chain alkyl group having a carbon number of 1 to 3, and each independently is preferably a hydrogen atom or a methyl group. Particularly preferably, one of $R^1$ and $R^2$ is a hydrogen atom, and the other is a methyl group.

$R^3$ is a hydrogen atom, an alkyl group having a carbon number of 1 to 4, an alkoxyalkyl group, an aryl group, a halogen atom or a haloalkyl group, and a hydrogen atom, an alkyl group having a carbon number of 1 to 4, a lower alkoxyalkyl group such as a methoxymethyl group and the like, a halogen atom such as a chlorine atom, a fluorine atom and the like, or a lower haloalkyl group such as a lower fluoroalkyl group and the like is preferable. Particularly, a hydrogen atom, an alkyl group having a carbon number of 1 to 4, a chlorine atom or a haloalkyl having a carbon number of 1 to 4 is preferable. As the alkyl group having a carbon number of 1 to 4, a methyl group and an ethyl group are preferable, and as the haloalkyl group having a carbon number of 1 to 4, a trifluoromethyl group is preferable.

As $R^3$, a hydrogen atom, a methyl group or a trifluoromethyl group is most preferable.

In addition, $R^3$ may be substituted at any of the ortho (o), meta (m) and para (p) positions relative to the position of substitution of the main chain of the prostaglandin skeleton by a benzene ring. $R^3$ is particularly preferably substituted at the meta (m) position.

Embodiment of Preferable Compound of the Present Invention

In addition, preferable combinations of $R^1$, $R^2$ and $R^3$ in compound (1) of the present invention are as follows.

$R^1$ is a hydrogen atom, $R^2$ is a hydrogen atom, and $R^3$ is a hydrogen atom.

$R^1$ is a hydrogen atom, $R^2$ is a hydrogen atom, and $R^3$ is a methyl group.

$R^1$ is a hydrogen atom, $R^2$ is a hydrogen atom, and $R^3$ is a chlorine atom.

$R^1$ is a hydrogen atom, $R^2$ is a hydrogen atom, and $R^3$ is a trifluoromethyl group.

$R^1$ is a methyl group, $R^2$ is a hydrogen atom, and $R^3$ is a hydrogen atom.

$R^1$ is a methyl group, $R^2$ is a hydrogen atom, and $R^3$ is a methyl group.

$R^1$ is a methyl group, $R^2$ is a hydrogen atom, and $R^3$ is a chlorine atom.

$R^1$ is a methyl group, $R^2$ is a hydrogen atom, and $R^3$ is a trifluoromethyl group.

$R^1$ is a hydrogen atom, $R^2$ is a methyl group, and $R^3$ is a hydrogen atom.

$R^1$ is a hydrogen atom, $R^2$ is a methyl group, and $R^3$ is a methyl group.

$R^1$ is a hydrogen atom, $R^2$ is a methyl group, and $R^3$ is a chlorine atom.

$R^1$ is a hydrogen atom, $R^2$ is a methyl group, and $R^3$ is a trifluoromethyl group.

$R^1$ is a methyl group, $R^2$ is a methyl group, and $R^3$ is a hydrogen atom.

$R^1$ is a methyl group, $R^2$ is a methyl group, and $R^3$ is a methyl group.

$R^1$ is a methyl group, $R^2$ is a methyl group, and $R^3$ is a chlorine atom.

$R^1$ is a methyl group, $R^2$ is a methyl group, and $R^3$ is a trifluoromethyl group.

Furthermore, preferable combinations from among those mentioned above are as follows, since the selective EP4 agonist action is high.

$R^1$ is a methyl group, $R^2$ is a hydrogen atom, and $R^3$ is a methyl group.

$R^1$ is a hydrogen atom, $R^2$ is a methyl group, and $R^3$ is a methyl group. Moreover, most preferable combinations are as follows.

$R^1$ is a methyl group, $R^2$ is a hydrogen atom, and $R^3$ is a m-methyl group.

$R^1$ is a hydrogen atom, $R^2$ is a methyl group, and $R^3$ is a m-methyl group.

Production Method of Compound (1) of the Present Invention

Compound (1) of the present invention can be produced, for example, based on the methods described in JP-A-07-324081 and JP-A-08-217772 relating to the inventions made by the present inventors. For example, using Corey lactone as a starting material, ω chain is introduced at first, and the lactone is converted by fluorination into ω chain-containing difluoro Corey lactone. Then, an α chain unit is introduced by an addition reaction with an organometallic reagent having a tetrazole group at the terminal and a dehydrating reaction, or Wittig reaction using a phosphonium salt having a tetrazole group at the terminal, and the like, and the hydroxyl group is deprotected as necessary, whereby compound (1) can be synthesized.

Alternatively, difluoro Corey lactone is obtained by fluorination from Corey lactone as a starting material. Then, an α chain unit is introduced by an addition reaction with an organometallic reagent having a tetrazole group at the terminal and a dehydrating reaction, or Wittig reaction using a phosphonium salt having a tetrazole group at the terminal, and the like, ω chain is introduced, and the hydroxyl group is deprotected as necessary, whereby compound (1) can be synthesized.

Alternatively, compound (1) can also be synthesized by converting a carboxy group of the carboxylic acid derivative described in JP-A-07-324081 to a cyano group and converting the derivative to a tetrazole derivative.

Of these production methods, representative methods are specifically explained using the following chemical formulas.

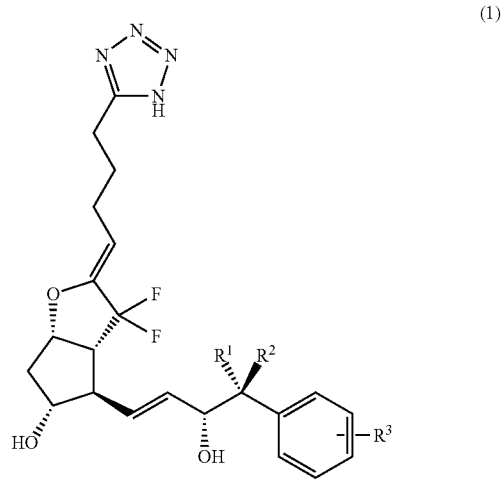

(1)

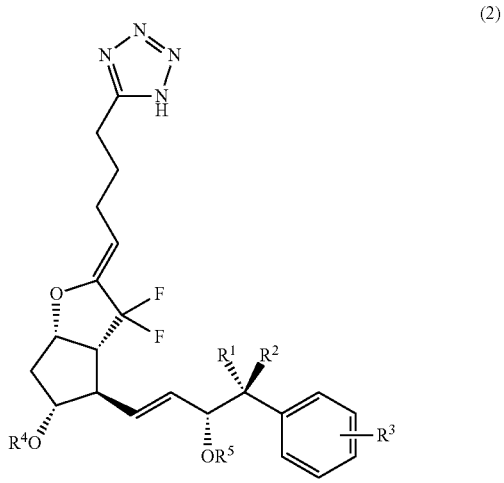

(2)

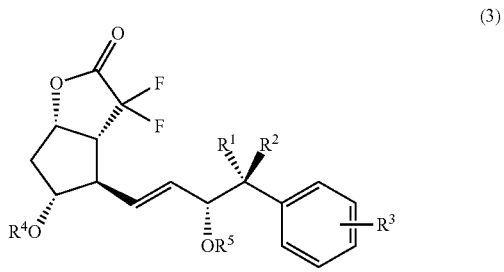

(3)

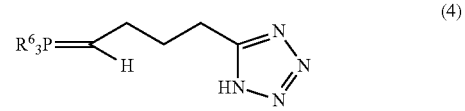

(4)

(5)

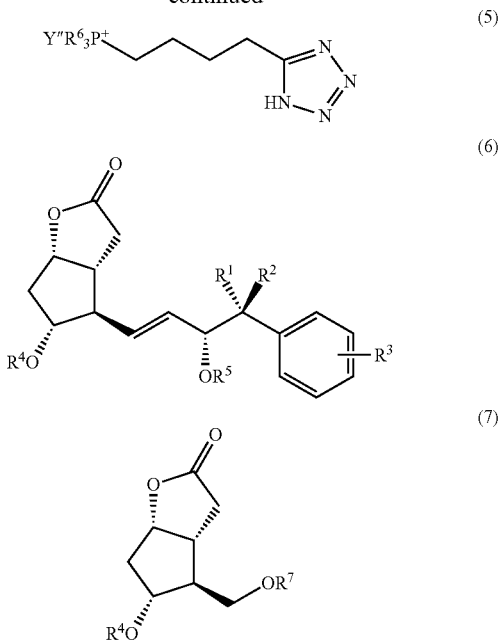

(6)

(7)

For example, using Corey lactone (7) as a starting material, ω chain is introduced at first, the obtained Corey lactone derivative (6) containing the ω chain is subjected to a fluorination reaction to give ω chain containing difluoro Corey lactone derivative (3) having two fluorine atoms at the α-position of the carbonyl group. Then, the difluorolactone derivative (3) is reacted with phosphorane derivative (4) to introduce an α chain unit, whereby $PGI_2$ derivative (2) with protected hydroxyl groups can be obtained. The hydroxyl-protecting group is removed to give compound (1) of the present invention.

The phosphorane derivative (4) can be obtained from a phosphonium salt derivative (5).

Except when $R^1$-$R^3$ are particular substituents, the above-mentioned lactone derivative (6) is a known compound. The above-mentioned novel lactone derivative (6) wherein $R^1$-$R^3$ are particular substituents can be produced by a method similar to that of known lactone derivatives (6). For example, novel lactone derivatives (6) can be produced by reacting 3-aryl-2-oxoalkylphosphonic acid diester with Corey lactone having a formyl group. Here, the alkyl chain of alkylphosphonic acid has a carbon number of not less than 3.

$R^4$, $R^5$ and $R^7$ are each independently a hydroxyl-protecting group. $R^4$, $R^5$, and $R^7$ may be same protecting groups. As the protecting group, the hydroxyl-protecting group described in "Shin Jikken Kagaku Koza (New Courses in Experimental Chemistry) 14, synthesis and reaction of organic compound (V)" (Maruzen Company, Limited), "Protective Groups in Organic synthesis" (by T. W. Greene, J. Wiley & Sons) and the like can be used. Specifically, a triorganosilyl group, an alkoxyalkyl group, a monovalent group having a cyclic ether structure and the like can be mentioned. As the triorganosilyl group, a silyl group wherein 3 groups selected from an alkyl group, an aryl group, an aralkyl group and alkoxy group are bonded to a silicon atom is preferable, and a group wherein 3 lower alkyl groups or aryl groups are bonded to a silicon atom is particularly preferable. As specific examples of the protecting group, a tetrahydropyranyl group, a tert-butyldimethylsilyl group, a tert-butyldiphenylsilyl group, a triethylsilyl group, a triphenylsilyl group or a triisopropylsilyl group and the like are preferable. Particularly, a tetrahydropyranyl group, a tert-butyldimethylsilyl group, a tert-butyldiphenylsilyl group and the like are preferable.

The hydroxyl-protecting group can be removed easily. The deprotection method of the protected hydroxyl group can be a conventional method. For example, the methods described in "Shin Jikken Kagaku Koza (New Courses in Experimental Chemistry) 14 synthesis and reaction of organic compound (I), (II) and (V)" (Maruzen Company, Limited), "Protective Groups in Organic synthesis" (by T. W. Greene, J. Wiley & Sons) and the like can be employed.

For conversion of lactone derivative (6) to difluorolactone derivative (3) by a fluorination reaction, various known fluorination methods can be applied. For example, a method including reacting with various electrophilic fluorinating agents in an inert solvent can be employed. The fluorination can also be performed by the methods described in JP-A-07-324081 and JP-A-09-110729 relating to the invention by the present inventors.

In the fluorination reaction of lactone derivative (6), an electrophilic fluorinating agent is preferably used. As the electrophilic fluorinating agent, known or well known electrophilic fluorinating agent can be used. For example, the electrophilic fluorinating agents described in "Chemistry of fluorine" (Kodansha Scientifics Ltd.) by Tomoya Kitazume, Takashi Ishihara, and Takeo Taguchi and the like can be mentioned. Specifically, N-fluorosulfonyl amides, N-sulfonyl imide derivative, acetyl hypofluorite, fluorine gas and the like can be mentioned.

The electrophilic fluorinating agent is preferably used in the presence of an inert solvent. As the inert solvent, ether solvents, hydrocarbon solvents, polar solvents, mixed solvents thereof and the like can be mentioned.

The difluorolactone derivative (3) obtained by the fluorination reaction is then reacted with phosphorane derivative (4) to give $PGI_2$ derivative (2) wherein the hydroxyl group is protected. The phosphorane derivative (4) is produced from the corresponding phosphonium salt derivative (5), in an inert solvent in the presence of a base, and the formed phosphorane derivative (4) is preferably used directly for the Wittig reaction with difluorolactone derivative (3) without isolation. As the production methods of phosphorane derivative (4) and phosphonium salt derivative (5), the methods described in DE2242239, DE2405255 and the like can be employed. As $R^6$ for phosphorane derivative (4) or phosphonium salt derivative (5), an aryl group such as a phenyl group, a tolyl group and the like is preferable, and a phenyl group is particularly preferable. As the inert solvent, ether solvents, hydrocarbon solvents, polar solvents, aqueous solvents, alcoholic solvents, mixed solvents thereof and the like can be mentioned.

The hydroxyl-protecting group is removed from the $PGI_2$ derivative (2) obtained by the above method to give compound (1).

Since compound (1) of the present invention has an asymmetric carbon in the structure, various stereoisomers and optical isomers are present. The present invention encompasses all of such stereoisomers, optical isomers, and mixtures thereof.

Specific examples of compound (1) of the present invention include the compound represented by the following formula (8).

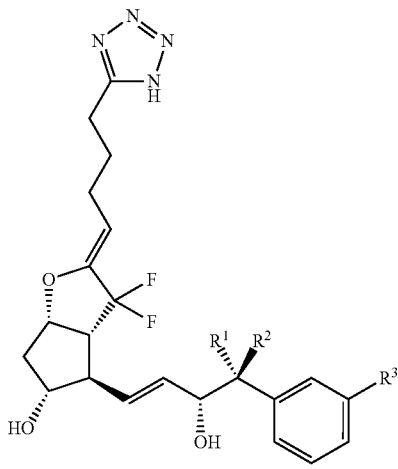

(8)

Examples of Compound (1) of the Present Invention

A compound wherein, in the formula (8), $R^1$, $R^2$, and $R^3$ have structures shown in the following Table 1 can be mentioned.

TABLE 1

|  | $R^1$ | $R^2$ | $R^3$ |
|---|---|---|---|
| Compound A | H | H | H |
| Compound B | H | H | Me |
| Compound C | H | H | Cl |
| Compound D | H | H | $CF_3$ |
| Compound E | Me | H | H |
| Compound F | Me | H | Me |
| Compound G | Me | H | Cl |
| Compound H | Me | H | $CF_3$ |
| Compound I | H | Me | H |
| Compound J | H | Me | Me |
| Compound K | H | Me | Cl |
| Compound L | H | Me | $CF_3$ |
| Compound M | Me | Me | H |
| Compound N | Me | Me | Me |
| Compound O | Me | Me | Cl |
| Compound P | Me | Me | $CF_3$ |

Features of Compound (1) of the Present Invention

Compound (1) of the present invention is a $PGI_2$ derivative which is not easily metabolized in the body and has improved stability. Since the carboxy group of the PG skeleton is converted to a tetrazole group, it is not easily metabolized by β-oxidation, which is known as a common metabolic pathway of fatty acid such as prostaglandins. Therefore, it has a prolonged plasma half-life and can maintain an effective plasma concentration for a long time, as compared to a compound having a carboxy group of the PG skeleton. Since the metabolic stability is improved in this way, the bioavailability of drugs can be improved.

Compound (1) of the present invention or a pharmaceutically acceptable salt thereof shows an action of a selective EP4 agonist. Examples of preferable compound (1) showing such action are the same as the aforementioned preferable examples of compound (1).

Medicament Containing Compound (1) of the Present Invention or a Pharmaceutically Acceptable Salt Thereof as Active Ingredient The medicament of the present invention contains compound (1) and/or a pharmaceutically acceptable salt of compound (1), and further, a pharmaceutically acceptable carrier and, in some cases, other treatment components.

The medicament of the present invention contains compound (1) and/or a pharmaceutically acceptable salt of compound (1), or a hydrate thereof, and further, a pharmaceutically acceptable carrier and, in some cases, other treatment components.

When the prophylactic or therapeutic agent of the present invention is administered to patients, the daily dose varies depending on the age and body weight of patients, pathology and severity and the like. Generally, 0.0001-10 mg, preferably 0.01-1 mg, of the agent is desirably administered in one to several portions. For example, for oral administration, 0.001-3 mg is preferable, and 0.001-0.5 mg is particularly preferable. For intravenous administration, 0.0001-1 mg is preferable, and 0.001-0.1 mg is particularly preferable. The dose can be changed as appropriate depending on the disease and its condition. As the dosing regimen, an injection product of the agent may be desirably administered by continuous drip infusion.

For use as a medicament, the agent can be administered to the body by oral administration and parenteral administration (e.g., intravascular (intravenous, intraarterial) administration, subcutaneous administration, rectal administration etc.). Examples of the dosage form include oral dosage form such as tablet, capsule and syrup, parenteral dosage form such as liquid injection (solution, emulsion, suspension and the like), infusion, suppositories, nasal preparations, patches and inhalations. Oral dosage is particularly desirable.

A preparation in the aforementioned dosage form can be produced by mixing compound (1) of the present invention or a pharmaceutically acceptable salt thereof with additives necessary for formulation such as conventional carriers, excipients, binders and stabilizers, and formulating the mixture in a conventional method. For example, when the preparation is a powder, granule, tablet and the like, it can be produced by using any pharmaceutical carriers preferable for producing a solid dosage form, for example, excipients, lubricants, disintegrants, binders and the like.

These excipient may be, for example, inert diluents, such as calcium carbonate, sodium carbonate, lactose, calcium phosphate and sodium phosphate; granulating agent and disintegrant, such as cornstarch and alginic acid; binder, such as starch, gelatin and gum arabic, and lubricant, such as magnesium stearate, stearic acid and talc. The tablet may be uncoated or coated by a known technique to delay disintegration and absorption in the stomach and the intestine, thus ensuring a sustained release for a longer time. For example, a time delay material, such as glyceryl monostearate or glyceryl distearate may be used.

Compound (1) of the present invention may be provided as a hard gelatin capsule containing a mixture with an inert solid diluent, for example, calcium carbonate, calcium phosphate or kaolin. Alternatively, it may be provided as a soft gelatin capsule containing a mixture with a water miscible solvent, such as propylene glycol, polyethylene glycol and ethanol, or oils, such as peanut oil, liquid paraffin and olive oil.

When the preparation is syrup or liquid, stabilizers, suspending agents, corrigents, aromatic substances and the like may be appropriately selected and used for the production, for example. For injection manufacturing, an active ingredient is dissolved in distilled water for injection together with a pH adjuster such as hydrochloric acid, sodium hydroxide, lactose, sodium lactate, acetic acid, disodium hydrogen phosphate and sodium dihydrogen phosphate, and an isotonic agent such as sodium chloride and glucose, and injection is aseptically prepared. An inactive nonaqueous diluent such as propylene glycol, polyethylene glycol, olive oil, ethanol and polysorbate 80 may be used for formulation of the preparation. Moreover, mannitol, dextrin, cyclodextrin, gelatin and the like may be added, and the mixture is freeze-dried in vacuo to give an injection to be dissolved before use. For stabilization and improvement of drug delivery to a lesion, moreover, a liposome preparation or a lipid emulsion may be formulated by a known method and used as an injection.

In addition, a rectal dosage preparation may be produced by using a suppository base, such as cacao butter, fatty acid triglyceride, fatty acid diglyceride, fatty acid monoglyceride and polyethylene glycol. Furthermore, a water-soluble base, such as polyethylene glycol, polypropylene glycol, glycerol and glycerolgelatin, an oily base, such as white petrolatum, hard fat, paraffin, liquid paraffin, Plastibase, lanolin and purified lanolin, and the like may be adjusted to suitable viscosity and ointment for intrarectal administration can also be produced.

Compound (1) of the present invention or a pharmaceutically acceptable salt thereof can be administered topically to the skin or mucous membrane, i.e., transdermal or transmucosal administration. As general dosage forms for this purpose, gel, hydrogel, lotion, solution, cream, ointment, sprays, dressing agent, foam preparation, film, skin patch, oblate, implant, sponge, fiber, bandage, microemulsion and the like can be mentioned. As commonly-used carriers, alcohol, water, mineral oil, liquid paraffin, white petrolatum, glycerol, polyethylene glycol, propylene glycol and the like can be mentioned.

Compound (1) of the present invention can be mixed with cyclodextrin or an appropriate derivative thereof or a soluble polymer such as polyethylene glycol-containing polymer, for the purpose of use in any of the aforementioned dosage forms, and improving solubility, dissolution rate, bioavailability and stability. For example, drug-cyclodextrin complex and the like have been confirmed to be generally useful for most dosage forms and administration routes. Both inclusion and non-inclusion complexes can be used. As another method for direct complexation with drugs, cyclodextrin can also be used as an auxiliary additive, i.e., carrier, excipient or solubilizer. For these purposes, $\alpha$-, $\beta$- and $\gamma$-cyclodextrins and the like are generally used.

Pharmaceutically Acceptable Salt of Compound (1) of the Present Invention

A pharmaceutically acceptable salt of compound (1) of the present invention is a salt of the moiety of the tetrazole group of the derivative with a basic substance, which is a compound wherein the hydrogen atom of the tetrazole group is substituted by cation.

Examples of the cation include alkali metal cations such as $Na^+$ and $K^+$, metal cations (other than alkali metal cations) such as $\frac{1}{2} Ca^{2+}$, $\frac{1}{2} Mg^{2+}$, $\frac{1}{2} Zn^{2+}$ and $\frac{1}{3} Al^{3+}$, $NH_4^+$, ammonium cations of organic amine and amino acid such as triethanolamine, diethanolamine, ethanolamine, tromethamine, lysine and arginine, and the like. Preferable cation is sodium ion or potassium ion.

More particularly, the acceptable salt is a salt produced from a pharmaceutically acceptable nontoxic base such as inorganic base and organic base. As a salt derived from the pharmaceutically acceptable nontoxic inorganic base, lithium salt, copper salt, ferric salt, ferrous salt, manganic salt, manganese salt and the like can be mentioned in addition to the aforementioned sodium salt, potassium salt, calcium salt, magnesium salt, zinc salt, aluminum salt, ammonium salt and the like. Of these, sodium salt, potassium salt, calcium salt, magnesium salt and ammonium salt are preferable, and sodium salt and potassium salt are particularly preferable. A salt derived from a pharmaceutically acceptable nontoxic organic base includes salts with primary, secondary and tertiary amine, substituted amine including naturally occurring substituted amine, cyclic amine, and basic ion exchange resin. Other than the examples of the aforementioned organic amine and amino acid, isopropylamine, diethylamine, triethylamine, trimethylamine, tripropylamine, ethylenediamine, N,N'-dibenzylethylenediamine, 2-diethylaminoethanol, 2-dimethylaminoethanol, morpholine, N-ethylmorpholine, piperazine, piperidine, N-ethylpiperidine, betaine, caffeine, choline, glucamine, glucosamine, histidine, Hydrabamine, methyl glucamine, polyamine resin, procaine, purine, theobromine and the like can be mentioned.

Use of Medicament Containing Compound (1) of the Present Invention or a Pharmaceutically Acceptable Salt Thereof as an Active Ingredient A medicament containing compound (1) of the present invention or a pharmaceutically acceptable salt thereof as an active ingredient can be applied to a disease involving EP4, preferably a disease wherein a selective EP4 agonist action can mitigate the symptom. Specifically, it is useful for immune diseases, diseases of the digestive tract, cardiovascular diseases, cardiac diseases, respiratory diseases, neurological diseases, ophthalmic diseases, renal diseases, hepatic diseases, bone diseases, skin diseases and the like.

The immune disease in the present invention includes autoimmune diseases such as amyotrophic lateral sclerosis, multiple sclerosis, Sjogren's syndrome, rheumatoid arthritis and systemic lupus erythematosus, post-transplantation rejection and the like, and inflammatory diseases such as asthma, neuronal cell death, arthritis, lung injury, pulmonary fibrosis, emphysema, bronchitis, chronic obstructive pulmonary disease, hepatopathy, acute hepatitis, nephritis (acute nephritis, chronic nephritis), renal failure, systemic inflammation response syndrome, sepsis, hemophagocytic syndrome, macrophage activation syndrome, Still's disease, Kawasaki disease, burn, systemic granuloma, hypercytokinemia at dialysis, multiple organ failure, shock and psoriasis.

The disease of the digestive tract in the present invention includes inflammatory disease and ulcerative disease of the digestive tract, which is a disease with inflammation or ulcer in the epithelial, mucosal or submucosal tissues of the digestive tract, or abnormal proliferation or dysfunction of mucosal epithelium, and which is caused by physical stimuli, chemical stimuli such as by gastric juice, stimuli by drug such as non-steroidal anti-inflammatory drugs and steroids, immune diseases and autoimmune diseases of unknown etiology, mental diseases and the like.

The inflammatory disease of the digestive tract includes inflammatory bowel disease, particularly ulcerative colitis, Crohn's disease, which is a non-specific granulomatous inflammatory disease accompanied by fibrillization or ulceration, intestinal Behcet's disease and simple ulcer. The ulcerative disease of the digestive tract of the present invention includes stomatitis, aphthous stomatitis, esophagitis, esophageal ulcer, gastritis, gastric ulcer and small intestinal ulcer.

Moreover, gastritis and gastric ulcer include drug-induced gastritis, gastric ulcer, alcoholic gastritis and gastric ulcer, and the drug-induced gastritis and gastric ulcer include gastritis and gastric ulcer induced by a non-steroidal anti-inflammatory drug.

Small intestinal ulcer includes drug-induced small intestinal ulcer and alcoholic small intestinal ulcer, and the drug-induced small intestinal ulcer includes small intestinal ulcer induced by a non-steroidal anti-inflammatory drug.

Particularly, the medicament of the present invention is useful as a prophylactic or therapeutic agent for ulcerative colitis, Crohn's disease, gastritis, gastric ulcer or small intestinal ulcer.

The cardiovascular disease and cardiac disease include arteriosclerosis, angina pectoris, myocardial infarction, brain disorder caused by cerebral hemorrhage, brain disorder caused by cerebral infarction, brain disorder caused by subarachnoid hemorrhage, pulmonary arterial hypertension, peripheral arterial obstruction (arteriosclerosis obliterans, and thromboangiitis obliterans) and various symptoms (intermittent claudication with lumbar spinal stenosis, leg numbness, Raynaud's syndrome, erectile dysfunction, hemorrhoids etc.) attributed to peripheral circulatory disturbance.

The respiratory disease includes asthma, lung injury, pulmonary fibrosis, emphysema, bronchitis, and chronic obstructive pulmonary disease.

The neurological disease includes neuronal cell death, amyotrophic lateral sclerosis, multiple sclerosis and brain disorder (brain disorders caused by cerebral hemorrhage, cerebral infarction, and subarachnoid hemorrhage).

The ophthalmic disease includes glaucoma and ocular hypertension.

The renal disease includes glomerulonephritis, diabetic nephropathy, IgA nephropathy and renal ischemia-reperfusion injury.

The hepatic disease includes hepatitis, hepatopathy and hepatic ischemia-reperfusion injury.

The bone disease includes osteoporosis, bone fracture, and a postoperative recovery phase after osteotomy.

The skin disease includes pressure ulcer and wound.

Furthermore, a medicament containing compound (1) of the present invention or a pharmaceutically acceptable salt thereof as an active ingredient is also useful as a prophylactic and/or therapeutic agent for alopecia, calvities, or hearing disorder (e.g., hearing disorder caused by sound), or a cervical ripening (promoting) agent.

The present invention is explained in detail in the following by referring to specific examples, which are not to be construed as limitative.

Example 1

Synthesis of methyl (2R)-2-(m-tolyl)propionate

To (2R)-2-(m-tolyl)propionic acid (12.45 g) were added methanol (14.83 g) and concentrated sulfuric acid (6.46 g), and the mixture was stirred under refluxing for 6 hr. Then, the mixture was neutralized with 10% aqueous sodium carbonate solution, and extracted with hexane. After drying over magnesium sulfate, the residue was concentrated under reduced pressure to give the title compound (12.79 g). The structural property was as described below.

$^1$H-NMR (CDCl$_3$): δ 1.49 (d, J=7.0 Hz, 3H), 2.33 (s, 3H), 3.64 (s, 3H), 3.69 (dd, J=14.4, 7.3 Hz, 1H), 7.06-7.22 (m, 4H).

Example 2

Synthesis of dimethyl (3R)-2-oxo-3-(m-tolyl)butylphosphonate

To dimethyl methylphosphonate (1.97 g) was added tetrahydrofuran (THF) (25 mL), and the mixture was cooled to −78° C. n-Butyllithium (1.5 M hexane solution) (10 mL) was added, and the mixture was stirred for 1 hr. Then, a solution of methyl ester {methyl (2R)-2-(m-tolyl)propionate} synthesized in Example 1 (1.34 g) in THF (3.8 mL) was added at −78° C., and the mixture was stirred for 2 hr. The reaction was quenched with 25 mL of saturated aqueous sodium hydrogen carbonate, and the mixture was extracted with ethyl acetate. The extract was dried over magnesium sulfate, and concentrated under reduced pressure. The residue was purified by silica gel column chromatography (hexane/ethyl acetate 5:1-1:5) to give the title compound (1.63 g). The structural property was as described below.

$^1$H-NMR (CDCl$_3$): δ 1.39 (d, J=6.7 Hz, 3H), 2.34 (s, 3H), 2.84 (ddd, J=22.3, 14.1, 0.6 Hz, 1H), 3.18 (dd, J=22.3, 14.1 Hz, 1H), 3.76 (dd, J=19.3, 11.1 Hz, 6H), 4.00 (dd, J=13.8, 7.0 Hz, 1H), 7.01-7.24 (m, 4H).

Example 3

Synthesis of (1S,5R,6R,7R)-6-[(1E,4R)-3-oxo-4-(m-tolyl)-1-pentenyl]-7-benzoyloxy-2-oxabicyclo[3.3.0]octan-3-one Sodium hydride (55%) (8.75 g) was dispersed in 1,2-dimethoxyethane (DME) (300 mL) and the mixture was ice-cooled. A solution of phosphonate (dimethyl (3R)-2-oxo-3-(m-tolyl)butylphosphonate) (54.7 g) synthesized in Example 2 in DME (50 mL) was added, and the mixture was stirred for 1 hr. To the above-mentioned solution was added a solution of (1S,5R,6R,7R)-6-formyl-7-benzoyloxy-2-oxabicyclo[3.3.0]octan-3-one (50.0 g) in DME (400 mL), and the mixture was stirred for 1 hr. The reaction was quenched with 350 mL of 10% brine, and the mixture was extracted with ethyl acetate. The extract was dried over magnesium sulfate, and the residue was concentrated under reduced pressure. The concentrated crude product was recrystallized from t-butyl methyl ether to give the title compound (64.7 g). The structural property was as described below.

$^1$H-NMR (CDCl$_3$): δ 1.39 (d, J=7.0 Hz, 3H), 2.20-2.28 (m, 1H), 2.30 (s, 3H), 2.34-2.41 (m, 1H), 2.49-2.57 (m, 1H), 2.76-2.85 (m, 3H), 3.80 (q, J=7.0 Hz, 1H), 5.03 (t, J=5.3 Hz, 1H), 5.23 (q, J=5.3 Hz, 1H), 6.19 (d, J=15.5 Hz, 1H), 6.69 (dd, J=15.6, 7.6 Hz, 1H), 6.94-7.19 (m, 4H), 7.42-7.95 (m, 5H).

Example 4

Synthesis of (1S,5R,6R,7R)-6-[(1E,3R,4R)-3-hydroxy-4-(m-tolyl)-1-pentenyl]-7-benzoyloxy-2-oxabicyclo[3.3.0]octan-3-one A solution of enone{(1S,5R,6R,7R)-6-[(1E,4R)-3-oxo-4-(m-tolyl)-1-pentenyl]-7-benzoyloxy-2-oxabicyclo[3.3.0]octan-3-one} (147.0 g) synthesized in Example 3 in THF (1480 mL) was cooled to −40° C., (−)-B-chlorodiisopinocampheylborane (1.7 M hexane solution) (721 mL) was added, and the mixture was stirred under ice-cooling for 20 hr. Acetone (183 mL) was added and the mixture was stirred for 3 hr. Aqueous sodium hydrogen carbonate was added, and the mixture was extracted with t-butyl methyl ether. The extract was dried over magnesium sulfate, and concentrated under reduced pressure to give a crude title compound (649.9 g).

Example 5

Synthesis of (1S,5R,6R,7R)-6-[(1E,3R,4R)-3-hydroxy-4-(m-tolyl)-1-pentenyl]-7-hydroxy-2-oxabicyclo[3.3.0]octan-3-one The crude alcohol, {(1S,5R,6R,7R)-6-[(1E,3R,4R)-3-hydroxy-4-(m-tolyl)-1-pentenyl]-7-benzoyloxy-2-oxabicyclo[3.3.0]octan-3-one} (649.9 g) synthesized in Example 4 was dissolved in methanol (740 mL), potassium carbonate (116.3 g) was added, and the mixture was stirred at room temperature for 17 hr. Acetic acid was added to adjust to pH 7, methanol was evaporated, water was added, and the mixture was extracted with ethyl acetate. The extract was purified by silica gel column chromatography (hexane/ethyl acetate=4/1-0/1) to give the title compound (22.3 g). The structural property was as described below.

$^1$H-NMR (CDCl$_3$): δ 1.33 (d, J=7.0 Hz, 3H), 1.70 (s, 1H(OH)), 1.86 (ddd, J=11.3, 7.8, 3.2 Hz, 1H), 2.07 (d, J=4.4 Hz, 1H(OH)), 2.13-2.23 (m, 2H), 2.34 (s, 3H), 2.35-2.44 (m, 3H), 2.47 (d, J=3.8 Hz, 1H), 2.56 (dd, J=18.2, 9.7 Hz, 1H), 2.80 (q, J=7.0 Hz, 1H), 3.79-3.85 (m, 1H), 4.12-4.16 (m, 1H), 4.81 (dt, J=7.0, 3.2 Hz, 1H), 5.27 (ddd, J=15.7, 8.5, 0.6 Hz, 1H), 5.50 (dd, J=15.2, 6.8 Hz, 1H), 6.94-7.20 (m, 4H).

Example 6

Synthesis of (1S,5R,6R,7R)-6-[(1E,3R,4R)-3-t-butyldimethylsiloxy-4-(m-tolyl)-1-pentenyl]-7-t-butyldimethylsiloxy-2-oxabicyclo[3.3.0]octan-3-one To a solution of the diol, {(1S,5R,6R,7R)-6-[(1E,3R,4R)-3-hydroxy-4-(m-tolyl)-1-pentenyl]-7-hydroxy-2-oxabicyclo[3.3.0]octan-3-one} (988 mg) synthesized in Example 5 in N,N-dimethylformamide (DMF) (10 mL) were added at room temperature t-butyldimethylsilyl chloride (1.17 g) and imidazole (1.08 g), and the mixture was stirred for 2.5 hr. The reaction mixture was poured into saturated aqueous sodium hydrogen carbonate, and the mixture was extracted with hexane/ethyl acetate=2/1 mixture. The extract was dried over magnesium sulfate, concentrated under reduced pressure and purified by silica gel column chromatography (hexane/ethyl acetate 20:1-10:1) to give the title compound (1.56 g). The structural property was as described below.

$^1$H-NMR (CDCl$_3$): δ −0.09 (d, J=6.4 Hz, 6H), 0.02 (d, J=2.4 Hz, 6H), 0.86 (s, 9H), 0.89 (s, 9H), 1.27 (d, J=7.0 Hz, 3H), 1.86-1.92 (m, 1H), 1.96-2.02 (m, 1H), 2.32 (s, 3H), 2.31-2.47 (m, 3H), 2.62-2.73 (m, 2H), 3.82 (q, J=4.7 Hz, 1H), 4.05 (t, J=6.4 Hz, 1H), 4.86 (dt, J=8.0, 2.4 Hz, 1H), 5.16 (dd, J=15.5, 7.4 Hz, 1H), 5.30 (dd, J=15.7, 6.3 Hz, 1H), 6.90-7.16 (m, 4H).

Example 7

Synthesis of (1S,5R,6R,7R)-6-[(1E,3R,4R)-3-t-butyldimethylsiloxy-4-(m-tolyl)-1-pentenyl]-7-t-butyldimethylsiloxy-2-oxa-4,4-difluoro-bicyclo[3.3.0]octan-3-one Tetrahydrofuran (THF) (19 mL) was added to manganese bromide (1.48 g) and N-fluorobenzenesulfonimide (2.48 g), and the mixture was stirred for 30 min, and cooled to −78° C. A solution of the lactone, {(1S,5R,6R,7R)-6-[(1E,3R,4R)-3-t-butyldimethylsiloxy-4-(m-tolyl)-1-pentenyl]-7-t-butyldimethylsiloxy-2-oxabioyclo[3.3.0]octan-3-one} (0.5 g) synthesized in Example 6 in THF (5 mL) was added, a solution (0.5 M, 13 mL) of potassium bis(trimethylsilyl)amide in toluene was added and the mixture was warmed to 0° C. over 3.5 hr. The reaction mixture was poured into saturated aqueous sodium hydrogen carbonate, and the mixture was extracted with hexane/ethyl acetate=1/1 mixture. The extract was dried over magnesium sulfate, concentrated under reduced pressure and purified by silica gel column chromatography (hexane/ethyl acetate 20:1) to give the title compound (0.32 g). The structural property was as described below.

$^1$H-NMR (CDCl$_3$): δ −0.08-0.03 (m, 12H), 0.82 (s, 9H), 0.89 (s, 9H), 1.28 (d, J=7.0 Hz, 3H), 1.70-1.77 (m, 1H), 1.96-2.04 (m, 1H), 2.31 (s, 3H), 2.60-2.91 (m, 3H), 3.82-3.87 (m, 1H), 3.99-4.23 (m, 1H), 5.00 (t, J=6.4 Hz, 1H), 5.06 (dd, J=15.7, 7.8 Hz, 1H), 5.33 (ddd, J=15.9, 6.7, 1.2 Hz, 1H), 6.88-7.16 (m, 4H).

$^{19}$F-NMR (CDCl$_3$): −113.1 (d, J=279.3 Hz), −91.0 (dd, J=279.3, 25.9 Hz).

Example 8

Synthesis of 4-[(Z)-(1S,5R,6R,7R)-6-[(1E,3R,4R)-3-t-butyldimethylsiloxy-4-(m-tolyl)-1-pentenyl]-7-t-butyldimethylsiloxy-2-oxa-4,4-difluoro-bicyclo[3.3.0]octan-3-ylidene]-1-(tetrazol-5-yl)butane To a suspension of 4-(tetrazol-5-yl)butyltriphenylphosphonium bromide (14.0 g) in toluene (390 mL) was added a solution (0.5M, 120 mL) of potassium bis(trimethylsilyl)amide in toluene, and the mixture was stirred at 60° C. for 1 hr. A solution of the difluorolactone, {(1S,5R,6R,7R)-6-[(1E,3R,4R)-3-t-butyldimethylsiloxy-4-(m-tolyl)-1-pentenyl]-7-t-butyldimethylsiloxy-2-oxa-4,4-difluoro-bicyclo[3.3.0]octan-3-one} synthesized in Example 7 (4.32 g) in toluene (130 mL) was added at −10° C., and the mixture was stirred for 18 hr while warming the mixture to room temperature. Aqueous sodium hydrogen carbonate was added to quench the reaction, and the mixture was extracted with hexane/ethyl acetate-1/1 mixture. The extract was dried over magnesium sulfate, concentrated under reduced pressure and purified by silica gel column chromatography (hexane/ethyl acetate-5/1-0/1) to give the title compound (4.1 g). The structural property was as described below.

$^1$H-NMR (CDCl$_3$): δ −0.14-0.01 (m, 12H), 0.82 (s, 9H), 0.89 (s, 9H), 1.23-1.27 (m, 3H), 1.82-2.09 (m, 5H), 2.21-2.28 (m, 1H), 2.31 (s, 3H), 2.45-2.53 (m, 1H), 2.64-2.73 (m, 2H), 2.93-2.97 (m, 2H), 3.90 (dd, J=11.7, 5.3 Hz, 1H), 4.08-4.09 (m, 1H), 4.84-4.87 (m, 2H), 5.27 (dd, J=15.5, 7.8 Hz, 1H), 5.44 (dd, J=15.6, 6.2 Hz, 1H), 6.92-7.16 (m, 4H).

$^{19}$F-NMR (CDCl$_3$): −112.3 (d, J=253.4 Hz), −81.4 (dd, J=253.4, 18.7 Hz).

Example 9

Synthesis of 4-[(Z)-(1S,5R,6R,7R)-6-[(1E,3R,4R)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane THF (81 mL), water (81 mL) and acetic acid (244 mL) were added to the compound (4.1 g) synthesized in Example 8, and the mixture was stirred at 35° C. for 46 hr. Water (500 mL) was added and the mixture was extracted with chloroform. The extract was dried over magnesium sulfate, concentrated under reduced pressure and purified by silica gel column chromatography (hexane/ethyl acetate=1/5-0/1) and recrystallized from diethyl ether to give the title compound (1.1 g). The structural property was as described below.

$^1$H-NMR (CD$_3$OD): δ 1.30 (d, J=7.0 Hz, 3H), 1.69 (dddd, J=14.6, 7.6, 3.0, 2.6 Hz, 1H), 1.82-1.95 (m, 2H), 2.10-2.16 (m, 2H), 2.29 (s, 3H), 2.31-2.41 (m, 2H), 2.48-2.56 (m, 1H), 2.72 (q, J=7.0 Hz, 1H), 2.93 (t, J=7.6 Hz, 2H), 3.78 (q, J=7.6 Hz, 1H), 4.04-4.10 (m, 1H), 4.69 (dt, J=6.48, 2.96 Hz, 1H), 4.79 (dt, J=7.6, 5.0 Hz, 1H), 5.36-5.46 (m, 2H), 6.95-7.13 (m, 4H).

$^{19}$F-NMR (CD$_3$OD): −116.6 (d, J=250.5 Hz), −84.8 (ddd, J=251.9, 17.3, 14.4 Hz).

Example 10

Synthesis of dimethyl 2-oxo-3-(m-tolyl)butylphosphonate

Using racemate of 2-(m-tolyl)propionic acid and in the same manner as in the method of Examples 1-2, the title compound was synthesized. The structural property was as described below.

$^1$H-NMR (CDCl$_3$): δ 1.39 (d, J=7.2 Hz, 3H), 2.34 (s, 3H), 2.83 (dd, J=22.4, 14.4 Hz, 1H), 3.18 (dd, J=22.4, 14.0 Hz, 1H), 3.76 (dd, J=19.6, 11.2 Hz, 6H), 3.99 (dd, J=14.0, 6.8 Hz, 1H), 7.01-7.27 (m, 4H).

Example 11

Synthesis of (1S,5R,6R,7R)-6-[(1E,3R,4RS)-3-t-butyldimethylsiloxy-4-(m-tolyl)-1-pentenyl]-7-t-butyldimethylsiloxy-2-oxabicyclo[3.3.0]octan-3-one Using racemate of dimethyl 2-oxo-3-(m-tolyl)butylphosphonate and in the same manner as in the method of Examples 3-6, the title compound was synthesized. The structural property was as described below.

$^1$H-NMR (CDCl$_3$): δ −0.20-0.10 (m, 12H), 0.80-0.90 (m, 18H), 1.18-1.28 (m, 3H), 1.85-2.20 (m, 2H), 2.31 (s, 3H), 2.30-2.80 (m, 5H), 3.80-4.15 (m, 2H), 4.81-4.95 (m, 1H), 5.12-5.42 (m, 2H), 6.88-7.20 (m, 4H).

Example 12

Synthesis of (1S,5R,6R,7R)-6-[(1E,3R,4RS)-3-t-butyldimethylsiloxy-4-(m-tolyl)-1-pentenyl]-7-t-butyldimethylsiloxy-2-oxa-4,4-difluoro-bicyclo[3.3.0]octan-3-one Using (1S,5R,6R,7R)-6-[(1E,3R,4RS)-3-t-butyldimethylsiloxy-4-(m-tolyl)-1-pentenyl]-7-t-butyldimethylsiloxy-2-oxabicyclo[3.3.0]octan-3-one synthesized in Example 11 and in the same manner as in the method of Example 7, the title compound was synthesized. The structural property was as described below.

$^1$H-NMR (CDCl$_3$): δ −0.20-0.05 (m, 12H), 0.80-0.90 (m, 18H), 1.19-1.29 (m, 3H), 1.70-2.10 (m, 2H), 2.31 (s, 3H), 2.60-3.05 (m, 3H), 3.84-4.12 (m, 2H), 4.95-5.50 (m, 3H), 6.85-7.20 (m, 4H).

$^{19}$F-NMR (CDCl$_3$): −113.6-−112.8 (m), −91.7-−90.6 (m).

Example 13

Synthesis of 4-[(Z)-(1S,5R,6R,7R)-6-[(1E,3R,4RS)-3-t-butyldimethylsiloxy-4-(m-tolyl)-1-pentenyl]-7-t-butyldimethylsiloxy-2-oxa-4,4-difluoro-bicyclo[3.3.0]octan-3-ylidene]-1-(tetrazol-5-yl)butane Using (1S,5R,6R,7R)-6-[(1E,3R,4RS)-3-t-butyldimethylsiloxy-4-(m-tolyl)-1-pentenyl]-7-t-butyldimethylsiloxy-2-oxa-4,4-difluoro-bicyclo[3.3.0]octan-3-one synthesized in Example 12 and in the same manner as in the method of Example 8, the title compound was synthesized. The structural property was as described below.

$^1$H-NMR (CDCl$_3$): δ −0.15-0.05 (m, 12H), 0.80-0.89 (m, 18H), 1.20-1.28 (m, 3H), 1.80-3.05 (m, 14H), 3.90-4.15 (m, 2H), 4.85-4.95 (m, 2H), 5.23-5.58 (m, 2H), 6.90-7.20 (m, 4H).

$^{19}$F-NMR (CDCl$_3$): −113.0-−111.3 (m), −82.0-−80.7 (m).

Example 14

Synthesis of 4-[(Z)-(1S,5R,6R,7R)-6-[(1E,3R,4RS)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane Using 4-[(Z)-(1S,5R,6R,7R)-6-[(1E,3R,4RS)-3-t-butyldimethylsiloxy-4-(m-tolyl)-1-pentenyl]-7-t-butyldimethylsiloxy-2-oxa-4,4-difluoro-bicyclo[3.3.0]octan-3-ylidene]-1-(tetrazol-5-yl)butane synthesized in Example 13 and in the same manner as in the method of Example 9, the title compound was synthesized. The structural property was as described below.

$^1$H-NMR (CDCl$_3$): δ 1.15-1.35 (m, 3H), 1.80-3.00 (m, 11H), 2.29 (s, 3H), 4.05-4.20 (m, 2H), 4.75-4.85 (m, 2H), 5.35-5.70 (m, 2H), 6.95-7.25 (m, 4H).

$^{19}$F-NMR (CDCl$_3$): −114.5-−112.7 (m), −83.5-−81.8 (m).

Example 15

Synthesis of 5-[(Z)-(1S,5R,6R,7R)-6-[(1E,3R,4RS)-3-hydroxy-4-(m-tolyl)-1-pentenyl]-7-hydroxy-2-oxa-4,4-difluoro-bicyclo[3.3.0]octan-3-ylidene]pentanoic acid (carboxylate form)

Using (1S,5R,6R,7R)-6-[(1E,3R,4RS)-3-t-butyldimethylsiloxy-4-(m-tolyl)-1-pentenyl]-7-t-butyldimethylsiloxy-2-oxa-4,4-difluoro-bicyclo[3.3.0]octan-3-one synthesized in Example 12 and (4-carboxybutyl)triphenylphosphonium bromide, and in the same manner as in the method of Examples 8-9, the title compound was synthesized. The structural property was as described below.

$^1$H-NMR (CD$_3$OD): δ 1.17-1.30 (m, 3H), 1.63-2.79 (m, 11H), 2.29 (s, 3H), 3.75-4.12 (m, 2H), 4.66-4.85 (m, 2H), 5.40-5.58 (m, 2H), 6.95-7.15 (m, 4H).

$^{19}$F-NMR (CD$_3$OD): −118.3-−117.7 (d, J=250.4 Hz), −86.1-−85.3 (m).

Example 16

In Vitro Metabolic Stability of the Compound of the Present Invention

A mixture of the compound F and compound J of the present invention described in Table 1 (F:J=52:41, synthesized in Example 14), and a mixture of compounds wherein the tetrazole groups at C-1 of compound F and compound J are respectively substituted by carboxylic acid (referred to as carboxylate form, F:J=54:34, synthesized in Example 15) were tested.

First, a mitochondria fraction was prepared from the rat liver according to the following Reference A. Then, in reference to the method of YAMAGUCHI et al. described in the following References B and C, an NADPH-independent β oxidation reaction was studied. The reaction was carried out at 37° C. for 30 min, and stopped with a methanol solution containing a suitable internal standard substance. Each compound was quantified by the internal standard method using a high performance liquid chromatography mass spectrometry apparatus (LC-MS/MS). The compound residual ratio after metabolic reaction of compounds F, J and each carboxylate form thereof in rat mitochondria fraction is shown in the following Table 2 in average±standard deviation of 3 experiments.

TABLE 2

Table 2
Residual Ratio of Parent Compound after β-Oxidation Reaction

| Compound | Residual ratio (%) |
| --- | --- |
| Compound F | 91.6 ± 6.8 |
| Compound J | 90.1 ± 6.9 |
| Carboxylate form of Compound F | 27.8 ± 2.2 |
| Carboxylate form of Compound J | 44.1 ± 2.1 |

As is clear from the above-mentioned Table 2, representative compound F and compound J of the present invention are not subject to β oxidation in a mitochondria fraction.

REFERENCES

A) The Japanese Biochemical Society, ed., Biochemical Experiment Course 12 energy metabolism and biological oxidation (vol. 1), Tokyo Kagaku Dojin, p. 217-218, 1st ed. 2nd printing, published on Jul. 11, 1979.
B) Drug Metabolism And Disposition 23(11): 1195-1201 (1995).
C) Xenobiotica 26(6): 613-626 (1996).

Example 17

Plasma Pharmacokinetics after Intravenous Administration to Rats

To verify the in vivo metabolic stability of the compound of the present invention, plasma pharmacokinetics was evaluated after intravenous administration to rats. Male rats (6 weeks old, body weight 160-180 g) were acclimated for 1 week, and the animals diagnosed healthy were used. A mixture of compound F and compound J of the present invention described in Table 1 (F:J=52:41), and a mixture of carboxylate forms of compound F and compound J (F:J=54:34), and compound F (synthesized in Example 9) were dissolved in a small amount of ethanol and physiological saline was added to prepare test compound solutions. The test compound solutions were instantaneously administered intravenously at 1 mL/kg from the femoral vein of non-fasting rats under light ether anesthesia. Venous blood was drawn from the tail vein 5, 15, 30, 45, 60, 90 and 120 min after administration. The blood was mixed with heparin and centrifuged (3000 rpm, 4° C., 15 min) to obtain plasma. The plasma compound concentration was determined by the internal standard method using LC-MS/MS. The determination range by this method was from 0.1 to 100 ng/mL. The compound concentrations obtained from each rat were analyzed in a model-independent way using a pharmacokinetics analysis software WinNonlin (ver. 3.3), and average±standard deviation of 3 animals for each group was obtained. The apparent half-life ($t_{1/2}$) in the elimination phase is shown in the following Table 3.

TABLE 3

Table 3 Apparent Half-life of Elimination Phase of Compounds after Intravenous Administration to Rats

| test compound | dose | $t_{1/2}$ (min) |
| --- | --- | --- |
| compound F administered as a mixture with isomers | 50 μg/kg (mixture with isomers) | 115 ± 31 |
| compound J administered as a mixture with isomers | 50 μg/kg (mixture with isomers) | 77 ± 19 |
| compound F | 300 μg/kg | 158 ± 15 |
| carboxylate form of compound F administered as a mixture with isomers | 50 μg/kg (mixture with isomers) | 9.6 ± 1.7 |
| carboxylate form of compound J administered as a mixture with isomers | 50 μg/kg (mixture with isomers) | 8.9 ± 0.3 |

As is clear from the above-mentioned Table 3, $t_{1/2}$ values of the compound F and compound J of the present invention were about 1-2 hr, which were markedly prolonged in comparison with less than 10 min of the carboxylate forms. It suggests that the compound F and compound J of the present invention have excellent metabolic stability.

Example 18

Receptor Affinity

PG receptor affinity of compound F and compound J of the present invention was evaluated. Compound F used was one synthesized in Example 9, and compound J was prepared by separating and purifying the compound synthesized in Example 14 with a column (the same preparations were used in the following Examples). COS-7 cells were transfected with the genes of mouse EP4, human EP1-4 or human IP to overexpress the receptor and then the cell membranes were collected. As a labeled ligand, tritium-labeled $PGE_2$ was used for EPs; tritium-labeled iloprost, for IP. The dissociation constant Kd value was obtained and inhibition constant Ki value of each test compound was determined in a conventional method. As a reference control, $PGE_2$ was used for EPs; beraprost sodium (BPS), for IP.

As a result, the dissociation constant was almost identical to the literature values. As shown in Table 4, $PGE_2$ equivalently bound to EP1-4, and its selectivity for EP subtypes was not observed. BPS selectively bound to IP. Compounds F and J bound to mouse and human EP4s. The affinity of compound F for binding to human EP4 was higher by 60-fold or more than those to human EP1, EP2 and EP3 receptors, and 100-fold or more than that to IP. The binding affinity of compound J to human EP4 was 40-fold higher than that to human IP.

TABLE 4

Table 4 Binding Affinity of Test Compounds to Various Receptors

| Test Compound | Ki value (nmol/L) | | | | | |
| --- | --- | --- | --- | --- | --- | --- |
| | Mouse EP4 | Human EP1 | Human EP2 | Human EP3 | Human EP4 | Human IP |
| $PGE_2$ | 2.6 | 2.9 | 6.0 | 2.1 | 1.1 | — |
| BPS | — | 942 | 4989 | 946 | 6148 | 160 |
| Compound F | 68 | 610 | 570 | 410 | 6.6 | 670 |
| Compound J | 590 | 4600 | 5400 | 1500 | 83 | 3400 |

Example 19

Agonist Activity

The EP4 agonist activity of compound F and compound J of the present invention was evaluated in a conventional method. In brief, human EP4 gene and CRE-LUC reporter gene were transfected into COS-7 cells. The cells were treated with a test compound one day later, and incubated for 3 hr. The cells were washed, a luminescence substrate was added, and the luminescence intensity was measured for the agonist activity. As a reference control, $PGE_2$ was used and the maximum activity of $PGE_2$ was taken as 100%. The 50% effective concentration ($EC_{50}$) was calculated and the agonist activity of the test compound was compared.

As a result, as shown in Table 5, compounds F and J are EP4 agonists.

TABLE 5

Table 5 EP4 Agonist Activity of Test Compounds

| Test Compound | $EC_{50}$ (nmol/L) EP4 |
| --- | --- |
| $PGE_2$ | 0.68 |
| BPS | >1000 |
| Compound F | 3.33 |
| Compound J | 440 |

Each value is a geometric mean of three determinations.

Example 20

Inhibitory Effect on Platelet Aggregation

The inhibitory effect of compounds F and J, and carboxylate forms thereof on platelet aggregation was evaluated. The carboxylate forms were prepared by separating and purifying the compound synthesized in Example 15 with a column. Blood was drawn from 3 healthy volunteers using sodium citrate as an anticoagulant, and platelet-rich plasma was prepared. The platelet-rich plasma was treated with physiological saline or test compounds and, 2 min later, platelet aggregation was induced with adenosine diphosphate (ADP, final concentration 10 μmmol/L) and recorded with a platelet aggregation measurement apparatus (nephelometry). The maximum aggregation of the group treated with physiological saline was taken as 100%, the concentration required for 50% inhibition ($IC_{50}$) thereof was calculated, and the inhibitory effect was assessed.

As a result, as shown in Table 6, compounds F and J had a considerably weak inhibitory effect on aggregation as compared to the IP agonists (BPS and carboxylate forms).

TABLE 6

Table 6 Inhibitory Effect of Test Compounds on Human Platelet Aggregation

| Test Compound | $IC_{50}$ (nmol/L) |
| --- | --- |
| BPS | 36 |
| Compound F | 917 |
| Compound J | 2725 |
| Carboxylate form of Compound F | 120 |
| Carboxylate form of Compound J | 190 |

Each $IC_{50}$ value is a geometric mean of three volunteers.

Example 21

Effect on Blood Pressure and Heart Rate in Mice

Male ICR mice (5 weeks old, Japan SLC) were purchased, acclimated for 6 days and used for the test. The animals were treated and measured under isoflurane inhalation anesthesia (anesthesia introduced at 2.5%, maintained at 1.8-2.1%), while body temperature was kept at 37° C. with a Heat Controller (ATC-402, Unique Medical Co., Ltd.). A catheter for administration of test compounds was inserted into the left femoral vein, and another catheter was inserted into the right femoral artery and connected to a pressure transducer to record each parameter of hemodynamics.

Compound F, the carboxylate form of compound F and BPS were intravenously administered at a dose of 0.01 mg/5 mL/kg, and the effect on the mean blood pressure and heart rate was evaluated with computer software for the analysis of hemodynamics (Fluclet, Dainippon Sumitomo Pharma Co., Ltd.). To the control group was intravenously administered a solvent (1.2% ethanol solution) at 5 mL/kg in the same manner. The results are expressed as a ratio of change in each parameter before and after the drug administration. Three to 6 animals were used for each group, and the results were expressed as average±standard deviation.

Figure 1B:
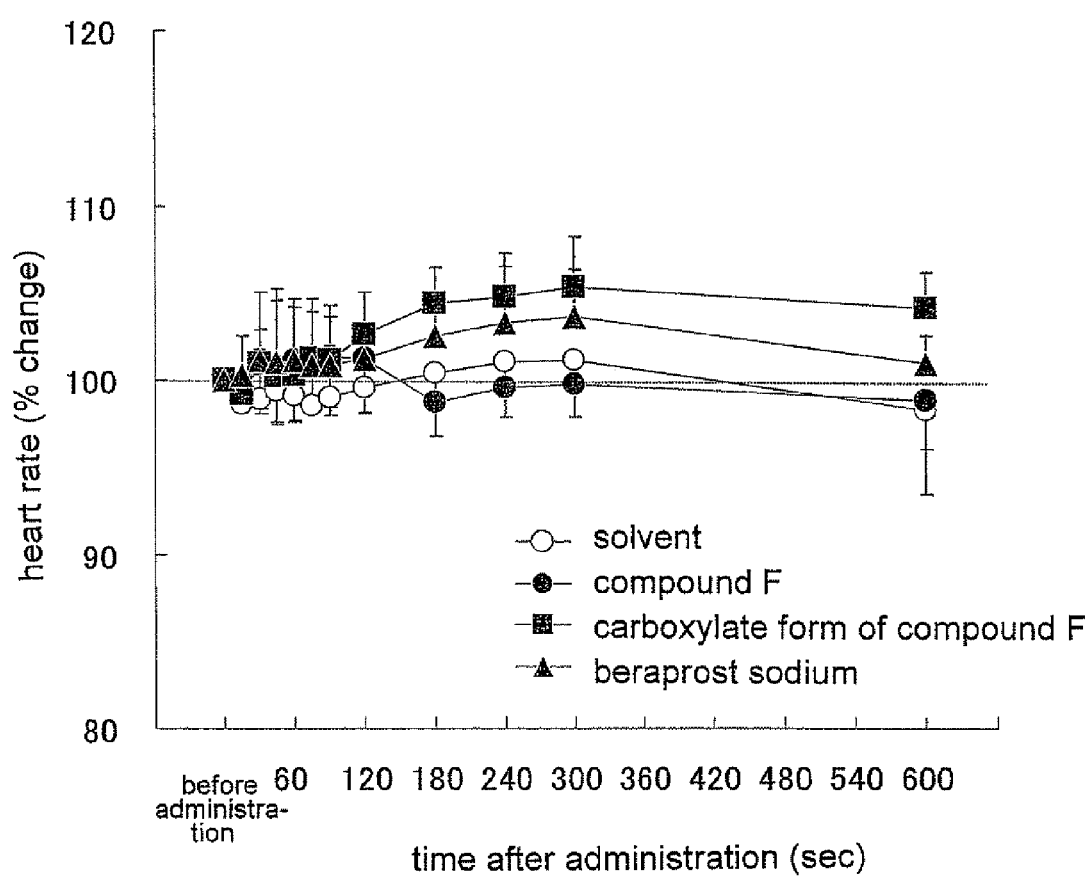
FIG. 1B shows the effect on heart rate in mice.

As a result, the solvent did not affect the mean blood pressure, but the carboxylate form of compound F and BPS remarkably decreased the blood pressure 1 min after the administration, at which time the maximum decrease ratio was 45% and 38%, respectively (FIG. 1A). The decreased blood pressure recovered in 10 min, but the heart rate was on the increase and remained high even after 10 min (FIG. 1B). The maximum decrease ratio by compound F was 16.2%, which was not significant (FIG. 1A). In addition, compound F had little effect on the heart rate (FIG. 1B). Therefore, the effect of compound F on the blood pressure and heart rate was extremely weak, as compared to the carboxylate form and BPS (IP agonist).

Example 22

Suppressive Effect on Inflammatory Cytokine Production

Using human peripheral blood, an anti-inflammatory effect of compounds F and J in vitro was studied. Blood was collected from 3 healthy volunteers, and CD4 positive T cells were prepared. Anti-CD3 antibody and anti-CD28 antibody were added, and 24 hr later the amounts of IL-2 and TNFα released in the medium were measured by ELISA. In addition, the collected whole blood was diluted with the medium, treated with indometacin to inhibit production of endogenous PGE2, and added with lipopolysaccharide. The amount of IP-10 released into the medium for 48 hr was measured with ELISA. In both cases, the test compound was added 30 min before stimulation. The production amount of the solvent control group was taken as 100% and the concentration required for 50% inhibition ($IC_{50}$) thereof was determined.

As a result, as shown in Table 7, $PGE_2$ and compound F strongly suppressed the production of inflammatory cytokines IL-2, TNFα and IP-10 even at an extremely low concentration. Although weak as compared to compound F, compound J also suppressed the cytokine production. The effect of each compound reflects its EP4 affinity and EP4 agonist activity.

As mentioned above, even though the compounds of the present invention including compound F are $PGI_2$ derivatives, they are EP4 selective agonists with an extremely reduced IP agonist activity compared with the activity observed in the carboxylate forms at C-1. The compound of the present invention is expected to show similar clinical efficacy in the disease group for which an EP4 agonist is effective. In contrast, the compound causes less concern of the side effects such as bleeding, hypotension, cardiac palpitation and face flush, since the effect thereof on the circulatory system due to the IP agonist action is also weakened. For example, it is important to attenuate such IP agonist actions in treatment of inflammatory bowel disease with intestinal bleeding. Using compound F, the efficacy of the compound of the present invention was determined in various animal models such as inflammatory bowel disease.

TABLE 7

Table 7 Suppressive Effect of Test Compounds on Cytokine Production

| Test Compound | $IC_{50}$ (nmol/L) | | |
|---|---|---|---|
| | IL-2 | TNF-α | IP-10 |
| $PGE_2$ | 0.062 | 0.447 | 0.168 |
| Compound F | 0.509 | 1.254 | 1.144 |
| Compound J | 64.0 | 89.5 | 102 |

Each value is a geometric mean of three volunteers.

Example 23

Prophylactic Effect on Dextran Sodium Sulfate-Induced Colitis Model in Mice

The prophylactic effect of compound F on ulcerative colitis was examined in dextran sodium sulfate-induced colitis model. The animal model displays inflammation localized to the large intestine, resulting in diarrhea and blood feces, which resembles pathologic condition of the clinical ulcerative colitis closely (cf.: References D and E).

Female BALE/c mice (6 weeks old, Japan SLC) were purchased, acclimated for 1 week and used for the study. Except the normal group, the mice were allowed to freely drink a dextran sodium sulfate (to be abbreviated as DSS, MP Biochemicals, M.W. 36,000-50,000, Lot No. 3439J) solution prepared to 2.2 w/v % for 9 days to induce colitis. Compound F was orally administered at doses of 0.1, 0.3 and 1 mg/kg, once a day, daily, from the start day of DSS drinking (day 0) to one day before autopsy (day 9). To the control group was orally administered a solvent (1 vol % ethanol solution) at 10 mL/kg in the same manner.

Our preliminary study had revealed that mouse feces show a correlation between the water content and shape thereof. Thus, to determine the level of diarrhea, the stool was graded into 6 levels; normal (score 0), spherical stool being not less than 50% (score 1), banana-shaped stool being less than 50% (score 2), banana-shaped stool being not less than 50% (score 3), muddy stool (score 4), watery stool (score 6) (stool consistency score). The fecal occult blood (including proctorrhagia) was graded using fecal occult blood slide 5 Shionogi II (Shionogi & Co., Ltd.) into 6 levels; negative (no change of the slide color from yellow, score 0), weakly positive (slightly blue green, score 1), positive (blue green, score 2), moderately positive (clear blue green, score 3), strongly positive (instantaneous color change to dark blue with color developer, score 4), and proctorrhagia (score 5). The sum of the stool consistency score and occult blood score was defined as the stool score. Eight to 10 animals were used for each group, and the results were expressed as average±standard deviation. On the day of autopsy, after laparotomy under ether anesthesia and blood collection, the mice were exsanguinated to death. Then the large intestines were dissected from just below the cecum to the anus and the length thereof was measured.

As a result, the body weight gradually increased over the study period without any difference among groups. The control group showed obvious loose stools and occult blood in stools from day 4 of DSS drinking. On the day of autopsy (day 9), the length of the large intestine thereof was clearly shorter than that of the normal group. Compound F dose-dependently suppressed the increase in the stool score, which was a suppressive tendency at 0.1 mg/kg and significant at 0.3 and 1 mg/kg (FIG. 2A). Likewise, compound F showed a dose-dependent suppressive effect on shortening of the large intestine (FIG. 2B). Thus, compound F clearly prevented the onset of ulcerative colitis.

REFERENCES

D) Lab. Invest. 69(2): 238-249 (1993).
E) Inflamm. Res. 45(4): 181-191 (1996).

Example 24

Effect of IP Agonist on Dextran Sodium Sulfate-Induced Colitis Model in Mice

Whether or not an IP agonist has an effect on such colitis model was determined using a selective IP agonist, BPS.

Female C57BL/6 mice (6 weeks old, Japan SLC) were purchased, acclimated for 1 week and used for the study. Except the normal group, the mice were allowed to freely drink a 3 or 2 w/v % DSS (MP Biochemicals, Lot No. 5653H and 5464H, respectively) solution for 1 week to induce colitis. BPS at a dose of 0.3 mg/kg and compound F at doses of 0.3 and 1 mg/kg were orally administered once a day, daily, from the start day of DSS drinking (day 0) to one day before autopsy (day 9). To the control group was orally administered a solvent (1 vol % ethanol solution) at 10 mL/kg in the same manner. The consistency of the stool was graded from score 0 to 4, with normal (0), partly loose stool (1), loose stool (2) and diarrhea (4). The blood feces was also graded from score 0 to 4, with normal (O), partly blood feces (1), blood feces (2) and blood feces plus proctorrhagia (4). The sum of both grades was defined as the stool score (maximum 8). Furthermore, the length of the large intestine was measured in the same manner as in Example 23. Six to 10 animals were used for each group, and the results are shown in average±standard deviation.

Figure 3A:
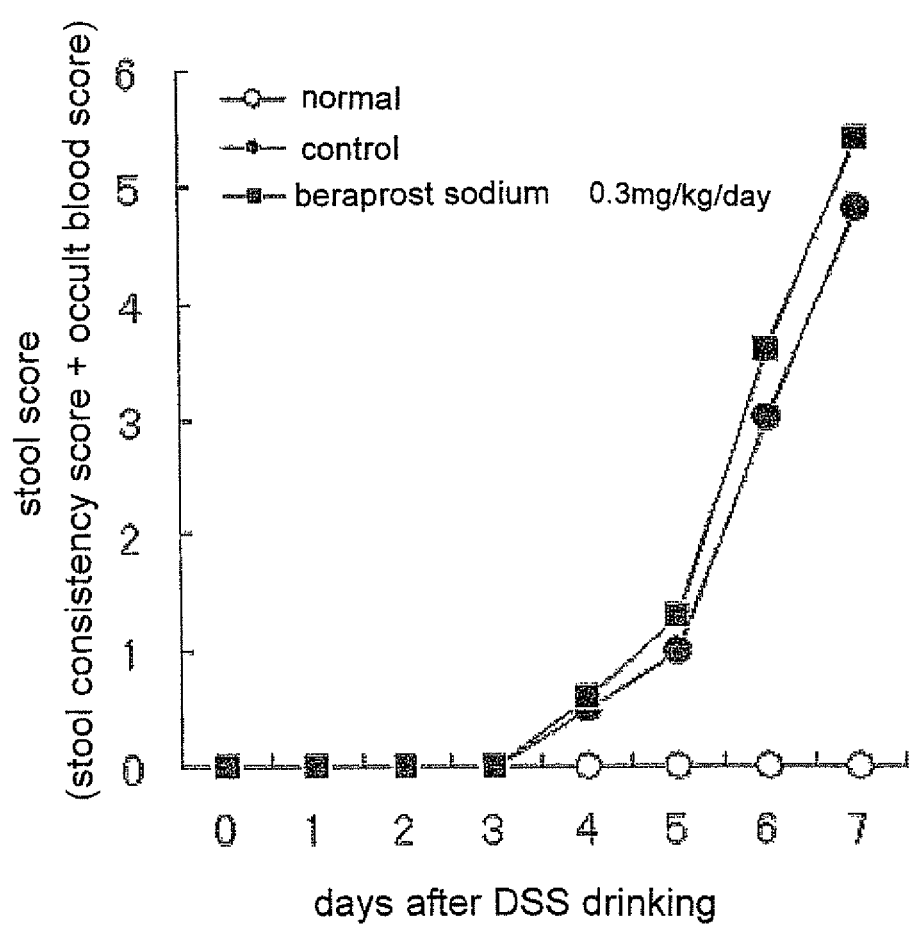
FIG. 3A shows the effect of BPS on abnormal stool in mouse (C57BL/6) DSS colitis model.
Figure 3B:
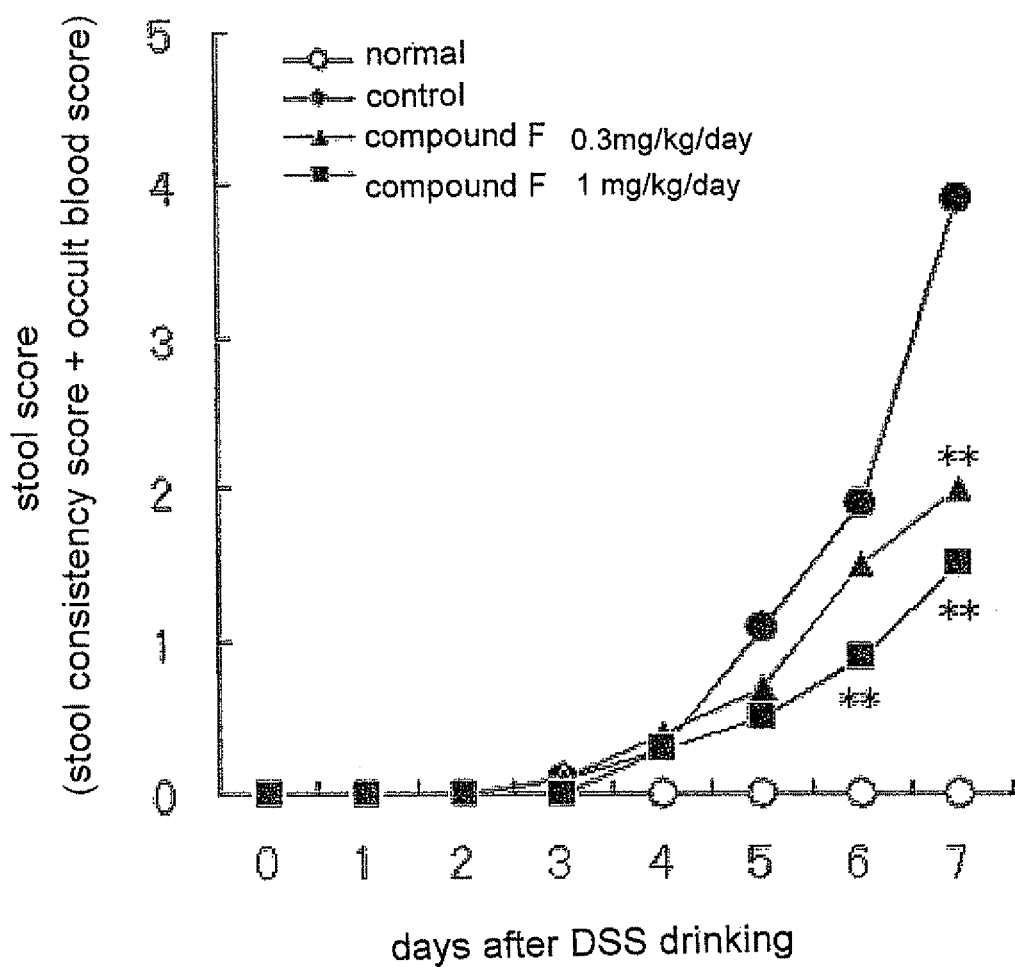
FIG. 3B shows the effect on abnormal stool in mouse (C57BL/6) DSS colitis model.
Figure 3C:
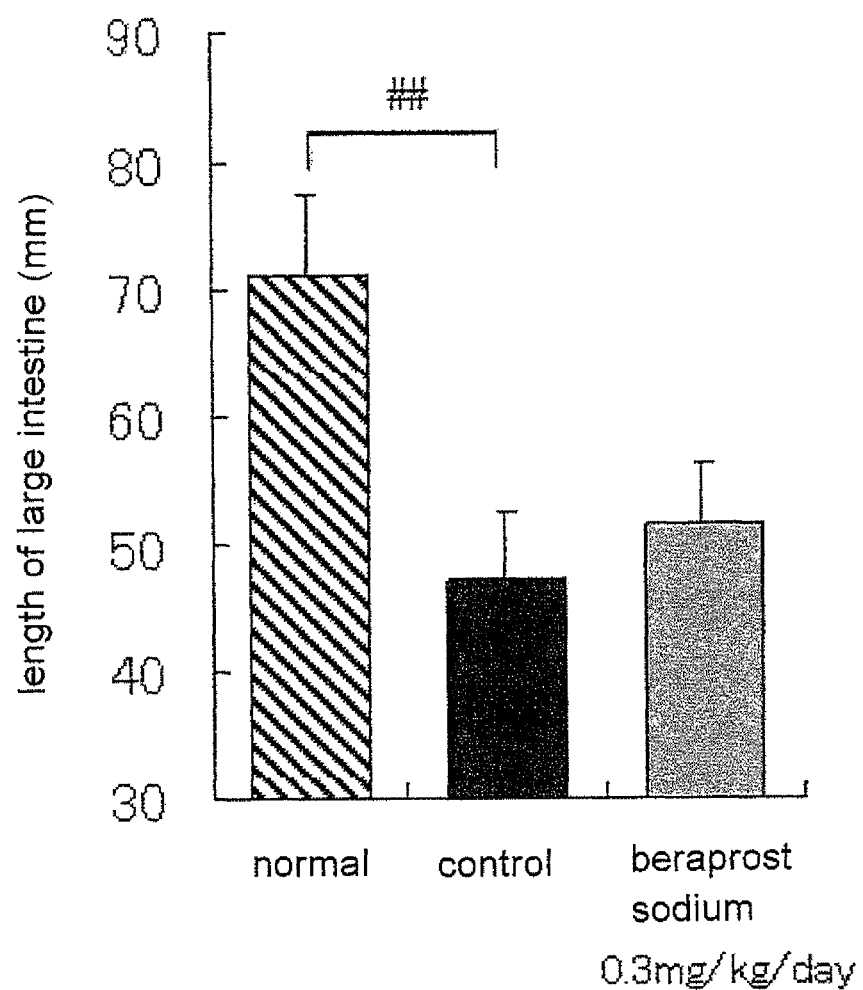
FIG. 3C shows the effect of BPS on colon shortening in mouse (C57BL/6) DSS colitis model.
Figure 3D:
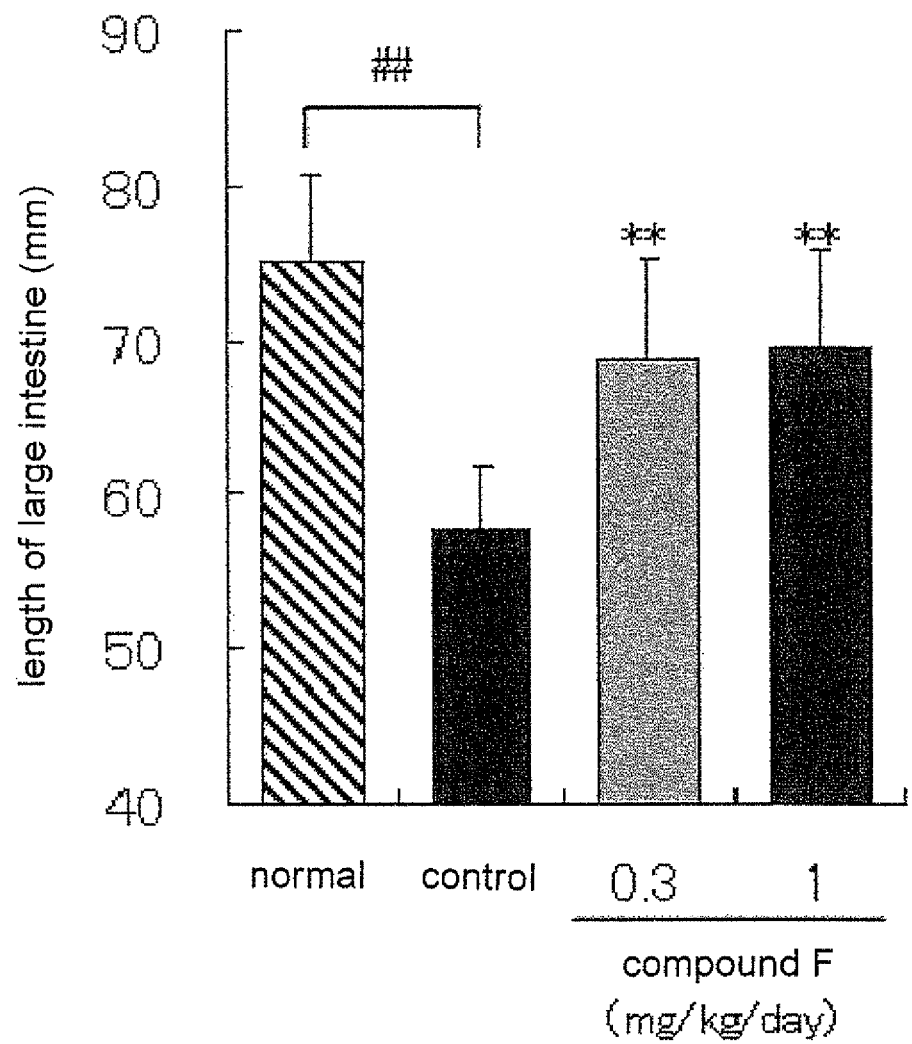
FIG. 3D shows the effect on colon shortening in mouse (C57BL/6) DSS colitis model.

As a result, the IP agonist BPS was not effective, but rather showed a tendency toward aggravation of the stool score. Also, it showed no effect on the shortening of the large intestine (FIGS. 3A and 3C). However, compound F demonstrated a superior prophylactic effect on the onset of colitis in the same manner as seen in Example 23 (FIGS. 3B and 3D). Thus, the treatment effect is brought by an EP4 agonist action, and is sometimes weakened by an IP agonist action. As such, being a selective EP4 agonist is important.

Example 25

Prophylactic Effect on Dextran Sodium Sulfate-Induced Colitis in Rats

Prophylactic effect of compound F on colitis was also studied in rats. Male SD rats, 7 weeks old, body weight around 210 g-240 g (Charles River) were purchased, acclimated for 1 week and used for the study. Except the normal group, the rats were allowed to freely drink a DSS (MP Biochemicals, M.W. 36,000-50,000, Lot No. 4556J) solution prepared to 5.5 w/v % for 8 days to induce colitis. Compound F at doses of 0.3, 1 and 3 mg/kg was orally administered once a day, daily, from one day before the start day of DSS drinking to one day before autopsy (day 7). To the control group was orally administered a solvent (1 vol % ethanol solution) at 5 mL/kg.

On day 8 from the start of DSS drinking, 1.25 w/v % Evans blue solution was administered at 0.2 mL/100 g from the tail vein. After 30 min, the rats were subjected to laparotomy under ether anesthesia and exsanguinated to death. Thereafter, the large intestine was dissected from just below the cecum to the anus, and the length was measured with a scale. After the contents of the large intestine were removed, the colonic tissue of 7 cm long from the anus was washed 3 times with physiological saline and dried overnight with a vacuum pump. The next day, the dry weight was measured, formamide (2 mL) was added, the dye was extracted at 50° C. overnight, and the level thereof was measured at 620 nm. A standard curve was prepared using an Evans blue standard solution, and the amount (mg) of Evans blue in 1 g of the colonic tissue was calculated to estimate degree of colonic tissue injury.

To show the level of diarrhea, the shape of stool was graded into 6 levels, with normal (score 0), rod-like stool being less than 50% (score 1), rod-like stool being not less than 50% (score 2), rod-like stool and partly muddy stool (score 3), muddy stool (score 4) and watery stool (score 6) (stool consistency score). Fecal occult blood was graded by the same method described in Example 23 (occult blood score). The sum of stool consistency score and occult blood score was defined as the stool score. Seven to 10 animals were used for each group, and the results are shown in average±standard deviation.

Figure 4A:
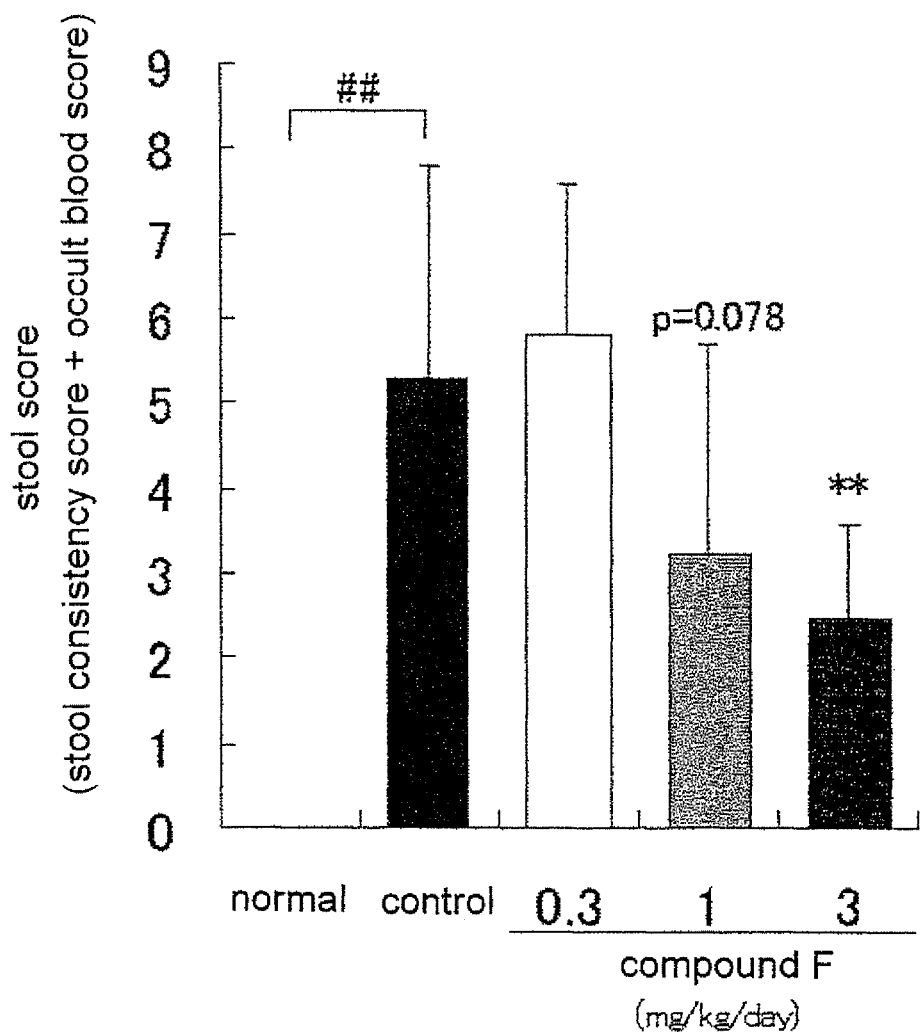
FIG. 4A shows the effect on abnormal stool in rat DSS colitis model.
Figure 4C:
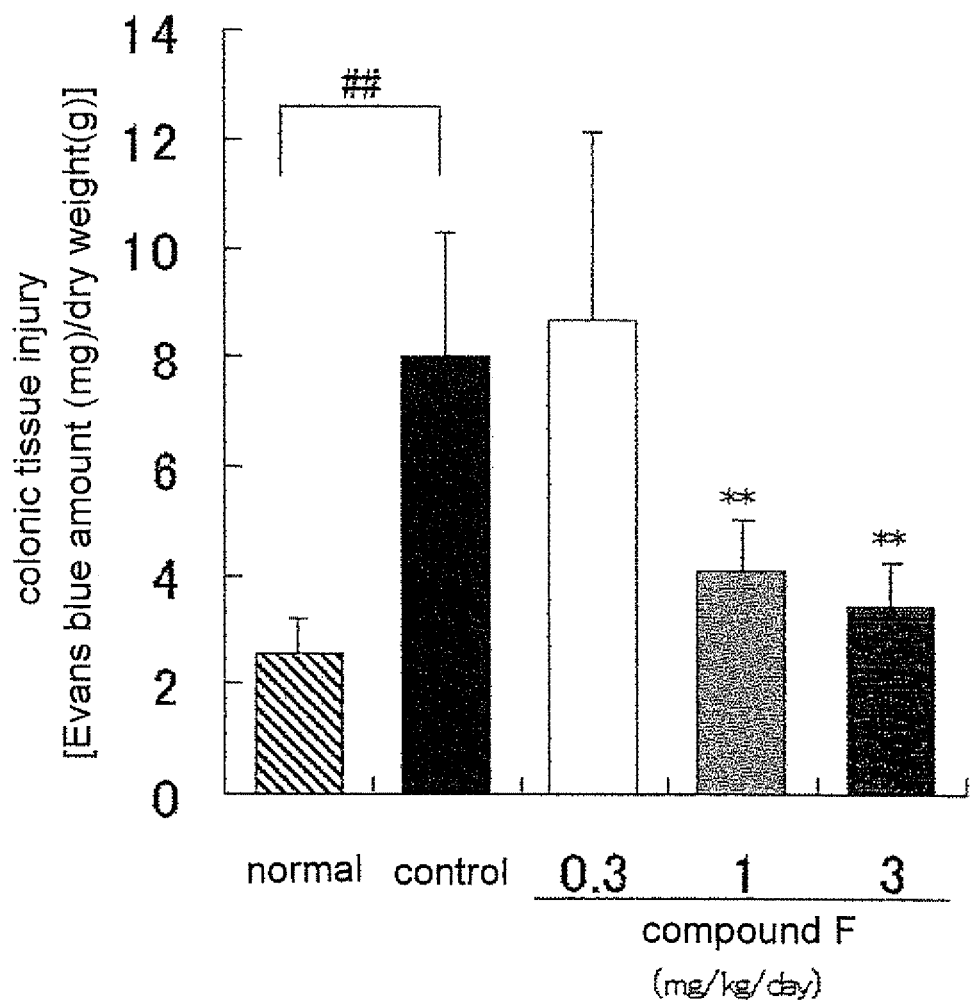
FIG. 4C shows the effect on colonic tissue injury in rat DSS colitis model.

As a result, the body weight of the control group gradually increased consistently, but the increase was significantly smaller than that of the normal group. The stool score of the control significantly elevated from day 1 of DSS drinking. On the day of autopsy (day 8), the large intestine thereof showed an apparent tissue injury and a significant shortening. In contrast, administration of compound F at 1 mg/kg and 3 mg/kg showed a suppressive tendency or significant suppressive effect on these events (FIGS. 4A, 4B, 4C). That is, compound F prevents ulcer development in the large intestine and normalizes the organ function, thereby leading suppression of symptoms of diarrhea and blood feces.

Example 26

Therapeutic Effect on Remission/Relapse Model of Dextran Sodium Sulfate-Induced Colitis in Mice Next, therapeutic effect of compound F on colitis was studied in a chronic model. Female BALB/c mice, 6 weeks old, body weight about 20 g (Japan SLC) were purchased, acclimated for 1 week and used for the study. The mice were divided into a colitis induction group and a normal group. The colitis induction group was allowed to freely drink a 2.6 w/v % DSS (MP Biochemicals, M.W. 36,000-50,000, Lot No. 45563) solution to induce colitis. On day 8 when the stool score (defined in Example 23) of the colitis induction group reached about 4.5, the mice were subdivided into a control group, a compound F 1 mg/kg administration group and a salazosulfapyridine (SIGMA, Lot No. 085K1930, hereinafter to be abbreviated as SASP) 100 mg/kg administration group. Then the mice were allowed to freely drink distilled water instead of DSS solution for 9 days (remission period). After the grouping, the stool score was evaluated every 3-4 days. When the score of the control group reached about 1, the mice were again allowed to drink the DSS solution to cause a relapse (relapse period). The periods of remission and relapse were taken as 1 cycle and the cycle was repeated 5 times. As for the 5th cycle, however, only the remission period was performed.

Compound F at a dose of 1 mg/kg and SASP at a dose of 100 mg/kg were orally administered once a day, daily, for 50 days from the initial remission period (day 8 from the start of 2.6 w/v % DSS drinking) to the fifth remission period (day 57 from the start of 2.6 w/v % DSS drinking). To the control group was orally administered a solvent (1 vol % ethanol solution) at 10 mL/kg. If a mouse had score 0 of both stool consistency score and occult blood score on the last day of each remission period, the mouse was regarded as "in remission". The remission ratio (%) was calculated as a ratio of mice in remission in each group. Eight to 10 mice were used for each is group and the results are shown in average value.

Figure 5:
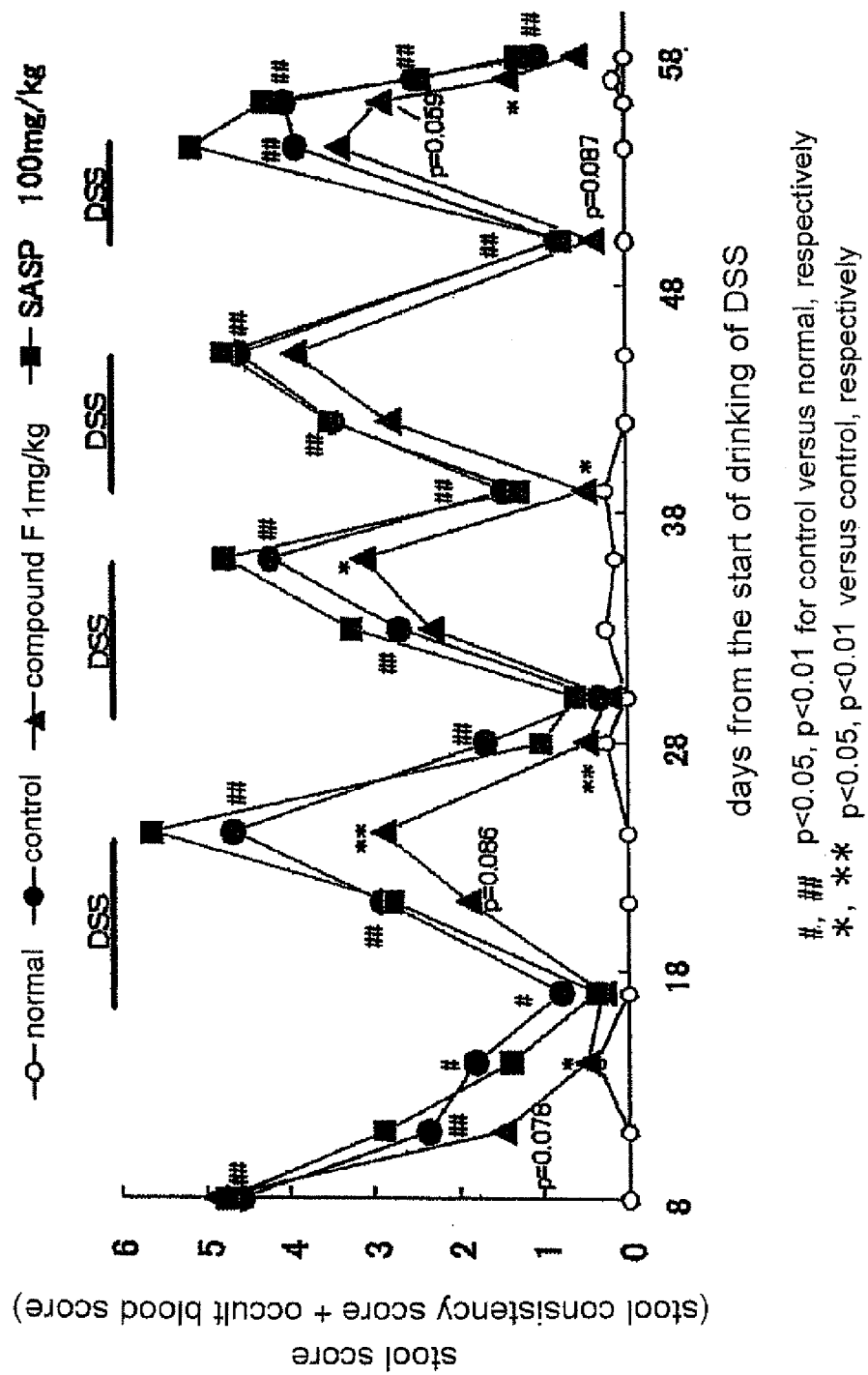
FIG. 5 shows the effect on abnormal stool in remission/relapse model of mouse DSS colitis.

As a result, the stool score of the control group increased in the relapse period, and decreased in the remission period. The score was significantly higher than that of the normal group almost throughout the study period (FIG. 5). The remission ratio thereof was 35.5% on average of 5 remission periods (Table 8). Compound F decreased the stool score early in the remission period, and suppressed an increase in the score in the relapse period. The remission ratio thereof was not less than 60% in any remission period, and the average was 66.0%, which was evidently higher than that of the control group. On the other hand, SASP did not show a clear effect on the stool score in either the remission period or the relapse period. The remission ratio thereof was slightly higher in the 1st, 3rd and 4th cycles than that of the control group, conversely lower in the 2nd and 5th cycles, and the average value was equivalent to that of the control group.

As shown above, compound F provides not only a prophylactic effect but also a therapeutic effect, as well as a remission maintaining effect. Moreover, the effects thereof are considered to be far superior to SASP in clinical use.

TABLE 8

Table 8 Remission Ratio of Remission/Relapse Model of DSS-induced Colitis in Mice

| Treatment | Number of animals | Remission Ratio (%) | | | | | |
|---|---|---|---|---|---|---|---|
| | | Cycle 1 | Cycle 2 | Cycle 3 | Cycle 4 | Cycle 5 | Average |
| Control | 9 | 33.3 | 66.7 | 11.1 | 33.3 | 33.3 | 35.5 |
| Compound F 1 mg/kg | 10 | 60.0 | 80.0 | 70.0 | 60.0 | 60.0 | 66.0 |
| SASP 100 mg/kg | 8 | 50.0 | 50.0 | 37.5 | 50.0 | 12.5 | 40.0 |

Example 27

Prophylactic Effect on $CD4^+CD25^-$ T Cell Transfer Colitis Model in Mice

The effect on Crohn's disease, another type of inflammatory bowel disease, was studied. T cell transfer model is well known as a Crohn's disease model, which develops chronic gastritis or enteritis (see: References F, G, H). In addition, it can also be regarded as an animal model of intestinal Behcet's disease or simple ulcer, suffering from similar intestinal ulcer accompanied by activation of T cells (see: References I, J).

Female BALB/cA Jcl mice, 6 weeks old, body weight 19-23 g (CLEA Japan, Inc.) and female C.B-17/Icr-scid mice (6 weeks old, CLEA Japan, Inc.) were purchased, acclimated for 1 week and used for the study.

After laparotomy under ether anesthesia, BALB/cA Jcl mice were exsanguinated to death through the abdominal aorta and caudal vena cava, and the spleen was isolated. Splenocytes were prepared from the spleen and then $CD4^+$ $CD25^-$ T cells were prepared with a $CD4^+$ T cell Isolation Kit (No. 130-090-860, Milky Biotech Co., Ltd.) and CD25-Biotin antibody (No. 130-092-569, Milky Biotech Co., Ltd.). The cells were separated using the autoMACS Separator (Milky Biotech Co., Ltd.). The separated $CD4^+CD25^-$ T cells were suspended in physiological phosphate buffer solution, and $2.5 \times 10^5$ cells per animal were intraperitoneally administered to C.B-17/Icr-scid mice to induce colitis.

One mg/kg of compound F or prednisolone was initially administered at 5 hr before transfer of $CD4^+CD25^-$ T cells, and orally administered thereafter once a day, daily, for 20 days. To the control group was orally administered a solvent (1 vol % ethanol solution) at 10 mL/kg. A clinical endpoint was the sum of stool consistency score (0-5), fecal occult blood score (0-4) and body weight decrease score (0-5), termed as the Disease Activity Index score (hereinafter to be abbreviated as DAY score: highest score 14). The stool consistency score was graded for the hardness of stool as normal (O), slightly loose (1), somewhat loose (2), loose (3), considerably loose (4) and diarrhea (5). The fecal occult blood score was evaluated in the same manner as in Example 23. The body weight decrease score was graded for the changes in the body weight as increase (O), decrease of less than 3% (1), decrease of not less than 3% and less than 6% (2), decrease of not less than 6% and less than 9% (3), decrease of not less than 9% and less than 12% (4), and decrease of not less than 12% (5). Eight to 10 mice were used for each group and the results were expressed as average.

Figure 6A:
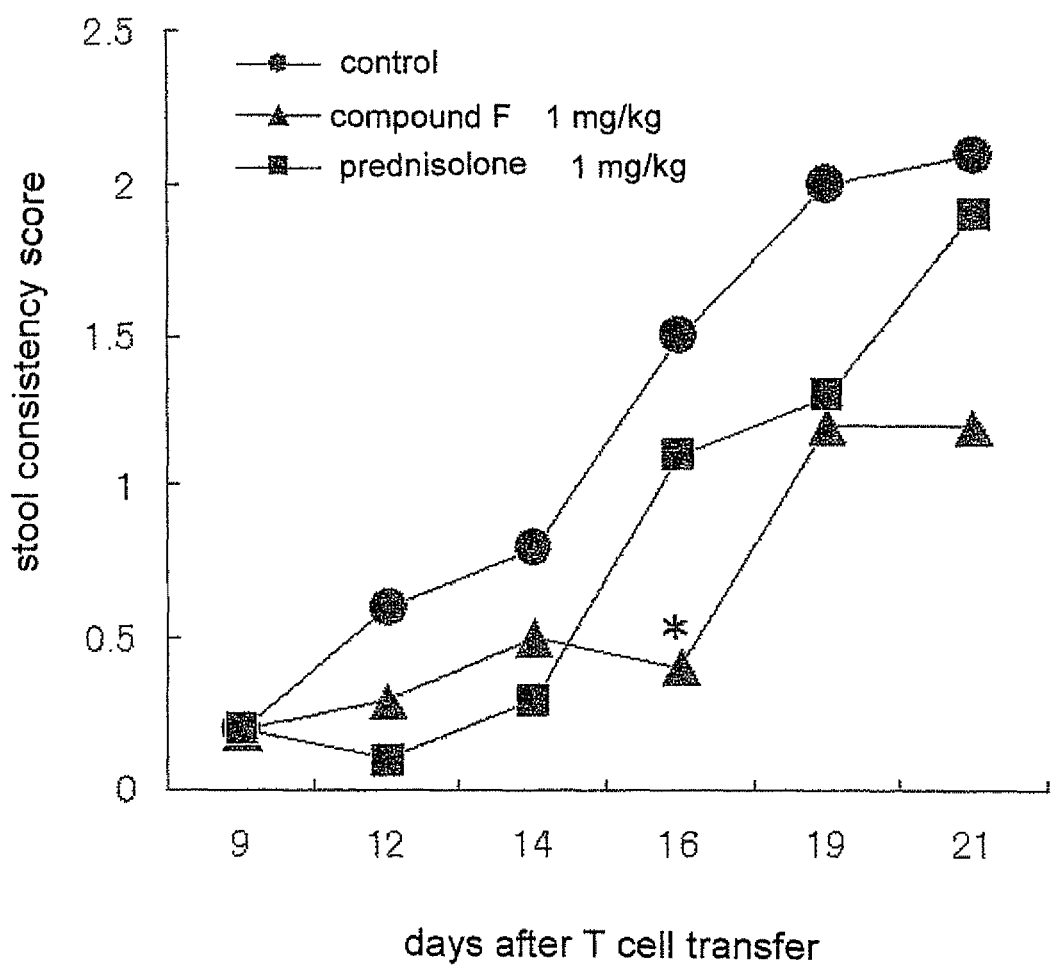
FIG. 6A shows the effect on stool consistency score in mouse T cell transfer model of colitis model.
Figure 6B:
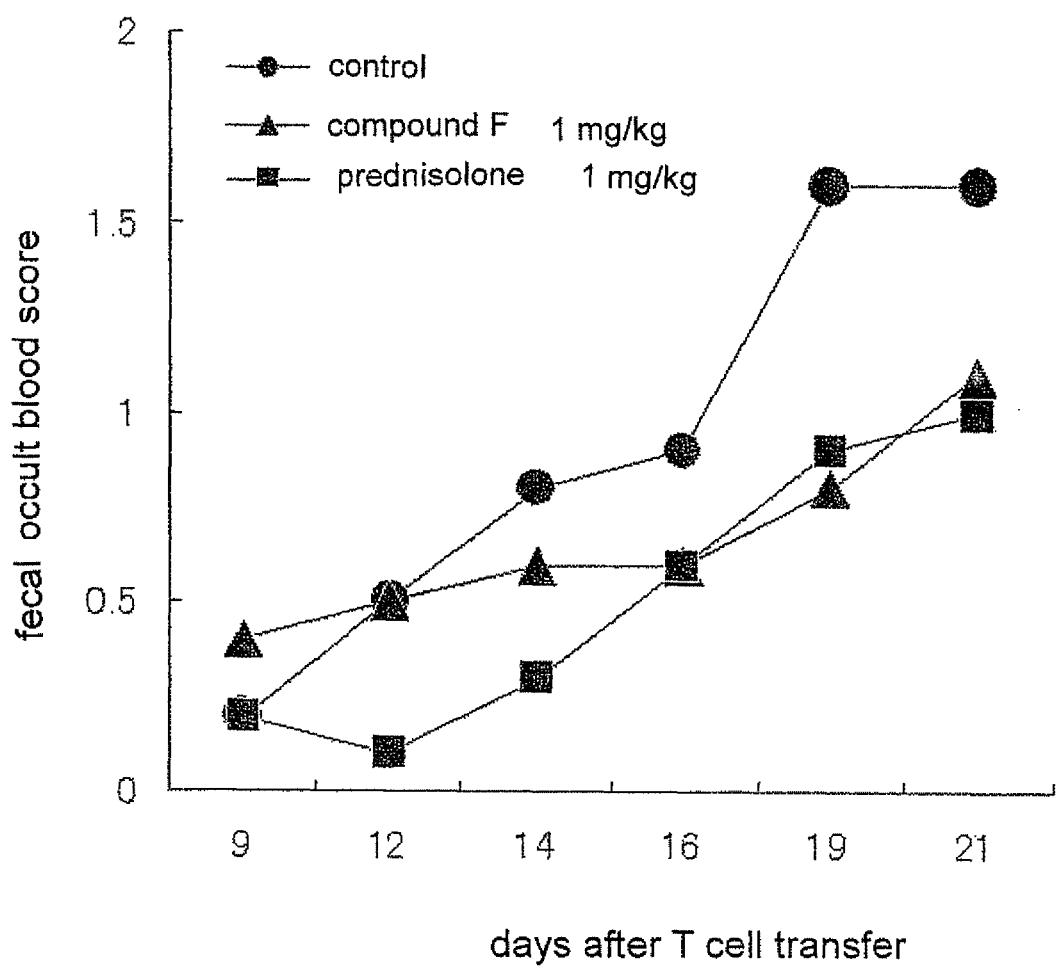
FIG. 6B shows the effect on fecal occult blood score in mouse T cell transfer model of colitis.
Figure 6C:
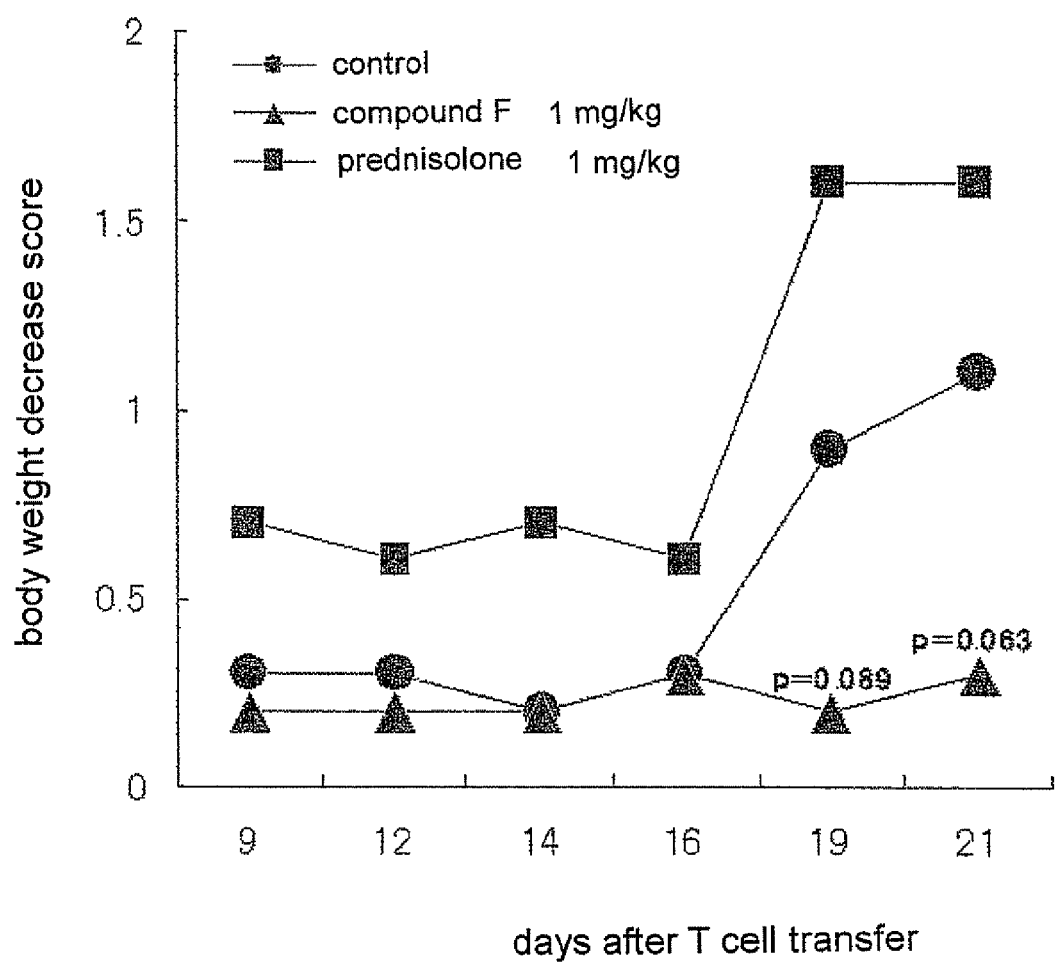
FIG. 6C shows the effect on body weight decrease score in mouse T cell transfer model of colitis.
Figure 6D:
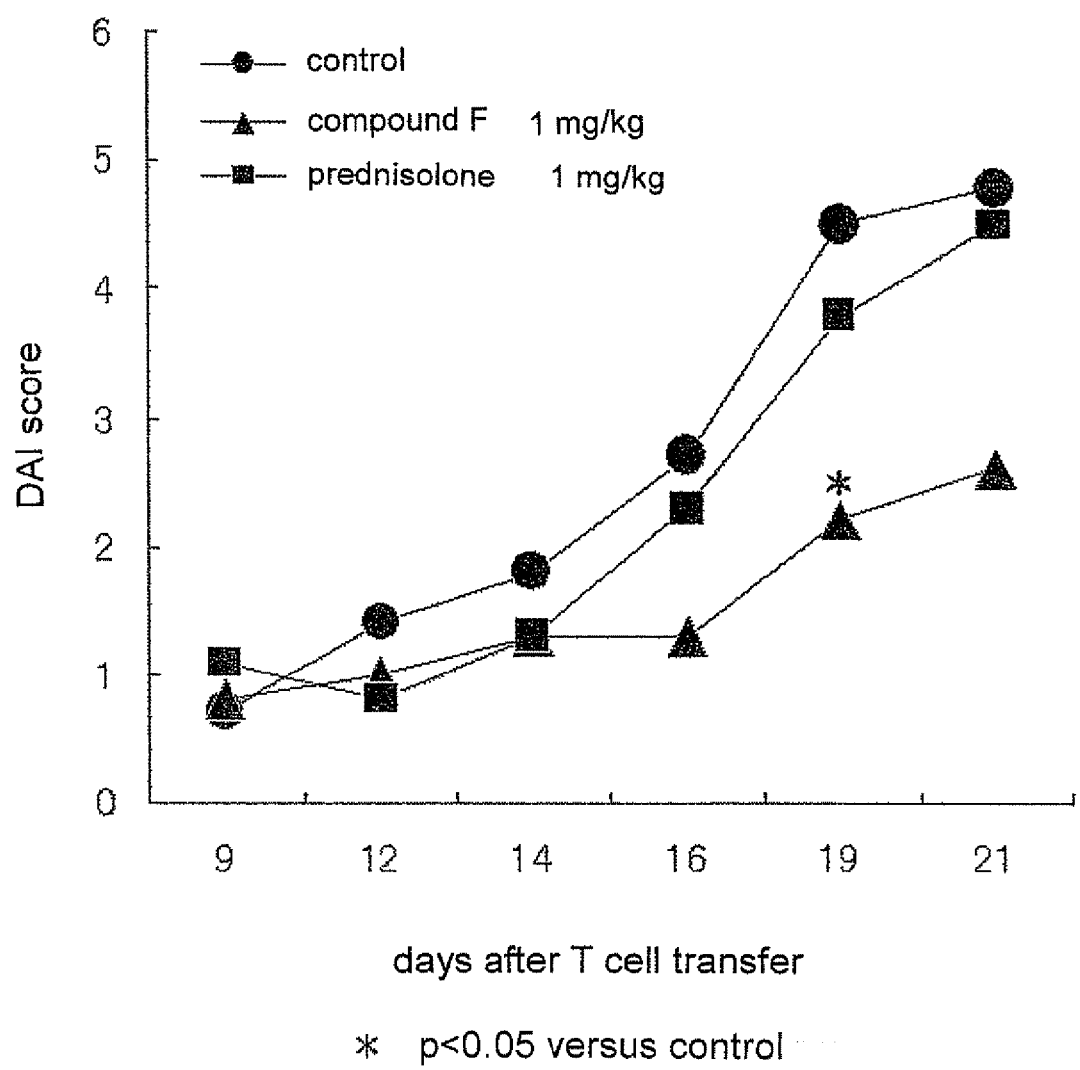
FIG. 6D shows the effect on DAI score in mouse T cell transfer model of colitis.

As a result, stool consistency score and fecal occult blood score of the control group showed a clear increase from 12 days after T cell transfer and the body weight decrease score showed a clear increase on day 19, all reaching almost maximum 21 days later. Compound F suppressed the increases in both the stool consistency score and the fecal occult blood score by almost half as shown in FIGS. 6A and 6B, respectively, and prevented the increase in the body weight decrease score almost completely as shown in FIG. 6C. On the other hand, though prednisolone suppressed an increase in the fecal occult blood score by almost the same level as the compound F administration as shown in FIG. 6B, it failed to show a clear effect on the stool consistency score on day 21 as shown in FIG. 6A. In addition, the body weight decrease score remained at higher values than those in the control group over the study period as shown in FIG. 6C, and prednisolone clearly worsened the score. As shown in FIG. 6D, the DAI score indicated that compound F is comprehensively superior to prednisolone.

Therefore, compound F can suppress the condition of Crohn's disease, intestinal Behcet's disease and simple ulcer is as well as ulcerative colitis more effectively than existing drugs.

REFERENCES

F) Immunol Rev. 182: 190-200 (2001).
G) Int. Immunopharmacol. 6(8): 1341-1354 (2006).
H) J. Immunol. 160(3): 1212-1218 (1998).
I) Clin. Exp. Immunol. 139(2): 371-378 (2005).
J) Histopathology. 45(4): 377-383 (2004).

Example 28

Effect on Ethanol-Induced Gastric Mucosal Injury Model in Rats

The suppressive effect of compound F on gastric mucosal injury was investigated in ethanol-induced gastric mucosal injury model in rats. This model is frequently used as an animal model of human acute gastritis associated with congestive mucosal injury (Reference K).

Male SD rats (7 weeks old, Charles River) were purchased through Oriental BioService Inc., acclimated for 1 week and used for the study. The rats were grouped based on the body weight, placed in a clean cage set with a wire mesh floor one day before the study, fasted for 19 hr (without water for last 3 hr), and orally administered with ethanol (special grade, Nacalai Tesque, Lot No. V8A5862, 1.5 mL) in all groups to induce gastric mucosal injury. Compound F was orally administered at doses of 0.01, 0.1 and 1 mg/kg 30 min before induction of gastric mucosal injury at a volume of 5 mL/kg. To the control group was orally administered a solvent (1 vol % ethanol solution) at 5 mL/kg in the same manner. Eight animals were used for each group.

The rats were bled to death from the abdominal aorta and caudal vena cava under ether anesthesia after 1 hr from the ethanol administration, and the stomach was isolated. The isolated stomach was immediately filled with 2 vol % neutral formalin solution (6 mL) and fixed for 15 min. The stomach was incised along the midline of the greater curvature from the cardiac part to the pyloric part, and extended on a vinyl chloride board. The length and width of each ulcer were measured under a stereomicroscope, the area was calculated, and the sum thereof was taken as the total ulcer area.

Figure 7:
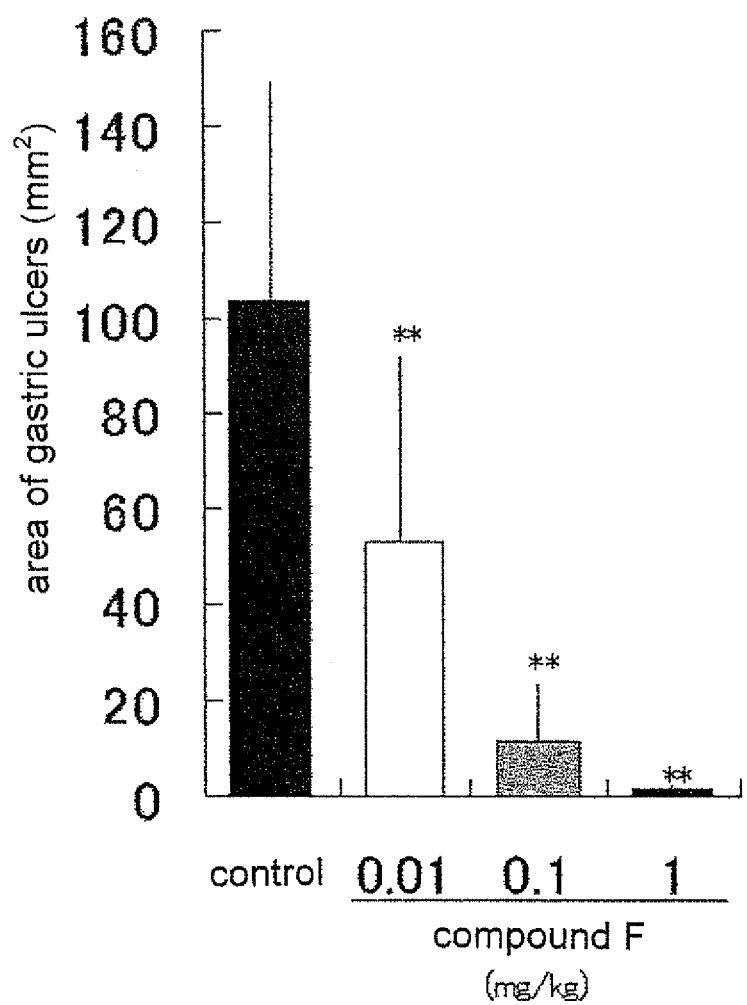
FIG. 7 shows the effect on gastric ulcer in rat ethanol induced-gastric mucosal injury model.

As a result, total ulcer area of the control group averaged 103 $mm^2$. Compound F significantly reduced the total ulcer area in a dose-dependent manner from 0.01 mg/kg, and almost completely reduced the area at a dose of 1 mg/kg (FIG. 7). Thus, compound F suppressed the gastric mucosal injury.

REFERENCE

K) Dig Dis Sci. 31 (2 Suppl), 81S-85S (1986).

Example 29

Effect on Indomethacin-Induced Small Intestinal Injury Model in Rats

The suppressive effect of compound F on small intestinal injury was investigated using indomethacin-induced small intestinal injury model in rats. Administration of non-steroidal anti-inflammatory drugs (NSAIDs) is known to induce hemorrhagic injury in the small intestine of human. This model is characterized by mucosal injury of the small intestine induced by administration of a NSAID, indomethacin, and shows pathology similar to that of NSAIDs-induced small intestinal injury in patients or Crohn's disease (References L and M).

Male SD rats, 7 weeks old (Charles River) were purchased, acclimated for 1 week and used for the study. The rats were grouped based on the body weight and subcutaneously administered with indomethacin (SIGMA, Lot No. 19F0018) at 15 mg/5 mL/kg to all groups to induce small intestinal injury. Compound F at doses of 0.01, 0.1 and 1 mg/kg was orally administered at a volume of 5 mL/kg 30 min before and 6 hr after the subcutaneous administration of indomethacin. To the control group was orally administered a solvent (1 vol % ethanol solution) at 5 mL/kg in the same manner. Eight animals were used for each group.

The rats were intravenously administered with 2 mL of 10 mg/mL Evans blue solution under ether anesthesia 23.5 hr after the indomethacin administration. After 30 min, the rats were bled to death from the abdominal aorta and caudal vena cava under ether anesthesia and the small intestine was isolated. The isolated small intestine was filled with an adequate amount (about 35 ml) of 2 vol % neutral formalin solution, and fixed for about 15 min. Thereafter, the small intestine was incised along the mesenteric attachment site, and extended on a vinyl chloride board. The length and width of each ulcer were measured under a stereomicroscope, the area was calculated, and the sum thereof was taken as the total ulcer area.

Figure 8:
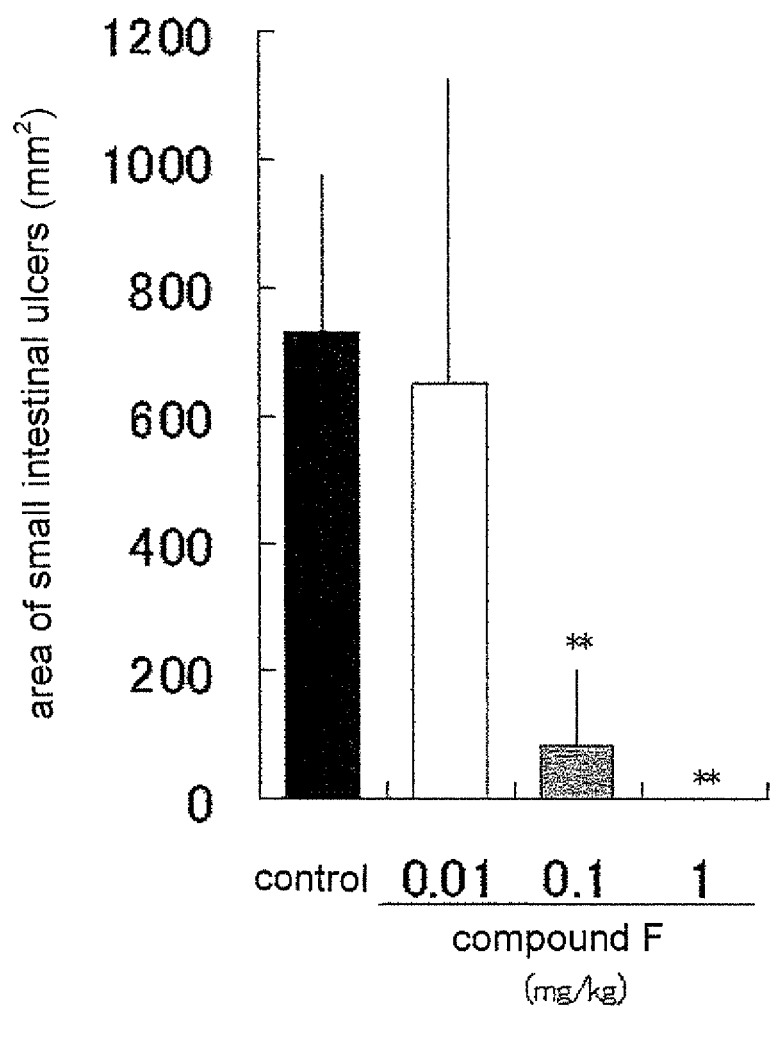
FIG. 8 shows the effect on small intestinal ulcer in rat indomethacin-induced small intestinal injury model.

As a result, the total ulcer area in the small intestine was about 730 $mm^2$ in the control group. In contrast, the compound F administration group significantly reduced the ulcer area in a dose-dependent manner from a dose of 0.1 mg/kg administration, and completely reduced the area at a dose of 1 mg/kg (FIG. 8). Thus, compound F strongly suppressed the small intestinal mucosal injury.

REFERENCES

L) Aliment Pharmacol Ther. 7(1), 29-39 (1993).
M) Acta Gastroenterol Belg. 57 (5-6), 306-309 (1994).

From the above, compound F showed a superior suppressive action on the direct injury to the gastrointestinal tract mucosa due to alcohol and the like and mucosal regenerative failure due to NSAIDs and the like. Therefore, compound F is expected to show a protective effect and a tissue repair effect on mucosal injury of the gastrointestinal tract.

As shown in the above-mentioned examples and found with compound F, the compound of the present invention is effective for gastrointestinal tract injury and delay in cure due to immune-related inflammation of digestive tract, drug-induced mucosal injury of the gastrointestinal tract and drug-induced mucosal regenerative failure. Specifically, it is useful for inflammatory bowel disease such as ulcerative colitis and Crohn's disease, alcoholic gastritis or gastric ulcer, small intestinal ulcer and the like. These actions are based on an EP4 agonist action, and are not limited to the recited diseases.

Example 30

Effect on Anti-Thy-1 Antibody-Induced Glomerulonephritis Model in Rats

Male Slc: Wistar rats (6 weeks old, Japan SLC) were purchased, acclimated for 1 week and used for the study. Except the normal group, anti-Thy-1 antibody (mouse anti-CD90 antibody (UK-Serotech Ltd. Code: MCA47XZ, clone No: MRC OX-7, Lot No. 0303)) was administered once intravenously to the animals. A mixture of compound F and compound J (F:J=52:41, indicated as compound F/J) was orally administered from the day of the antibody administration (day 0) to day 6, daily, twice a day (morning and evening; each 0.3 mg/kg). After 3 days from the antibody administration, urine was collected for one day. On day 7 of the antibody administration, the animal was autopsied. The right kidney was isolated, weighed and fixed with formalin. Five to 8 animals were used for each group and the results were expressed as average±standard deviation.

Figure 9A:
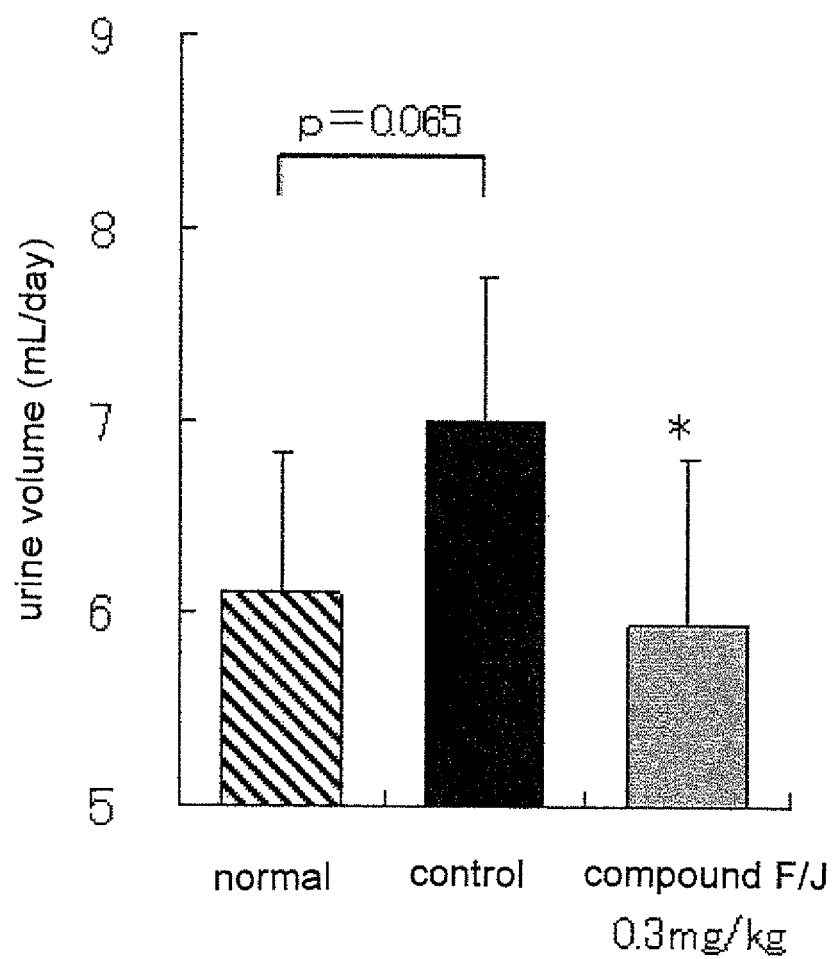
FIG. 9A shows the effect on urine volume in rat anti Thy-1 antibody-induced glomerulonephritis model.
Figure 9B:
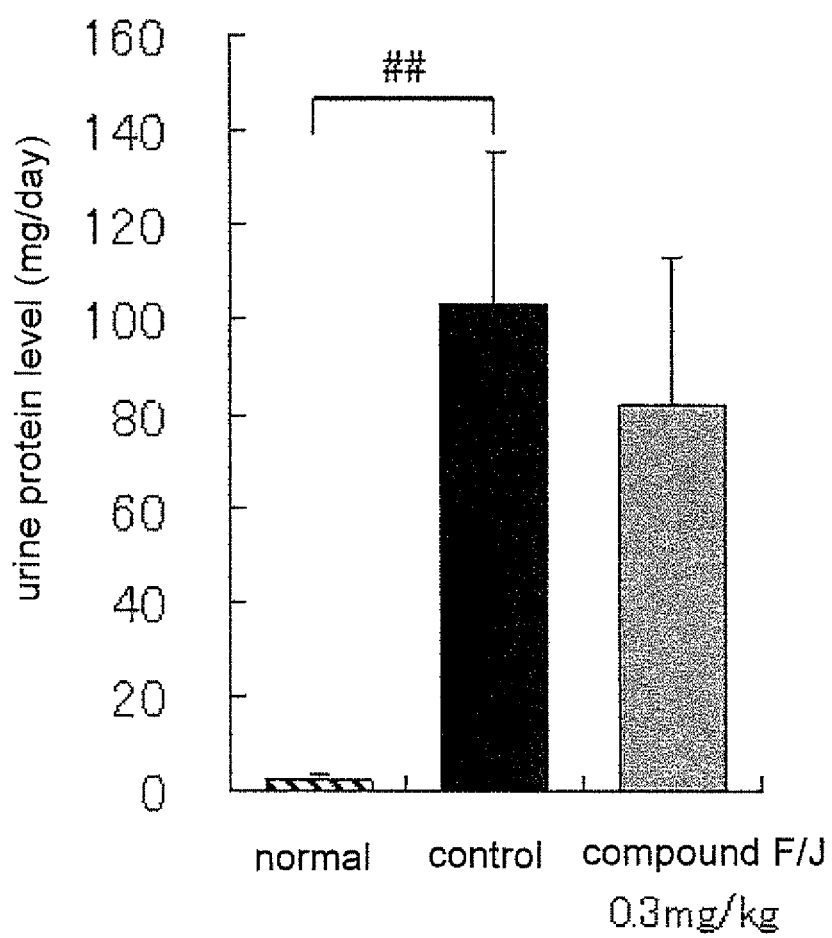
FIG. 9B shows the effect on the amount of urine protein in rat anti Thy-1 antibody induced glomerulonephritis model.
Figure 9C:
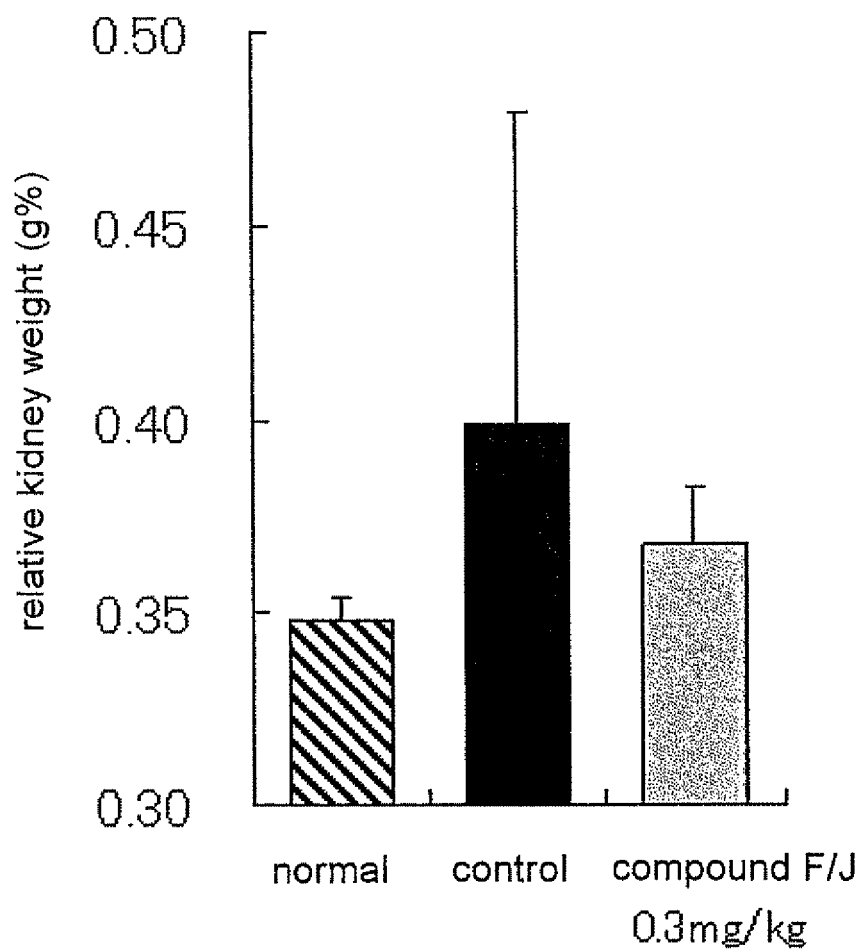
FIG. 9C shows the effect on relative kidney weight in rat anti Thy-1 antibody-induced glomerulonephritis model.
Figure 9D:
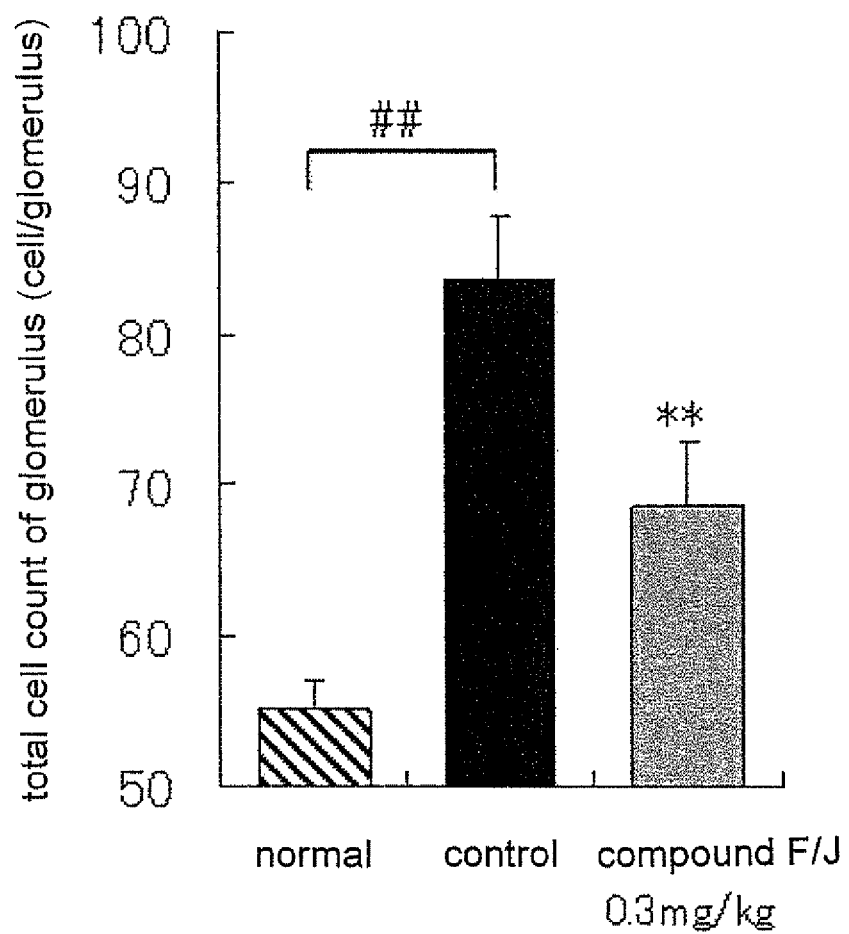
FIG. 9D shows the effect on renal histopathology (total glomerular cell count) in rat anti Thy-1 antibody-induced glomerulonephritis model.
Figure 9E:
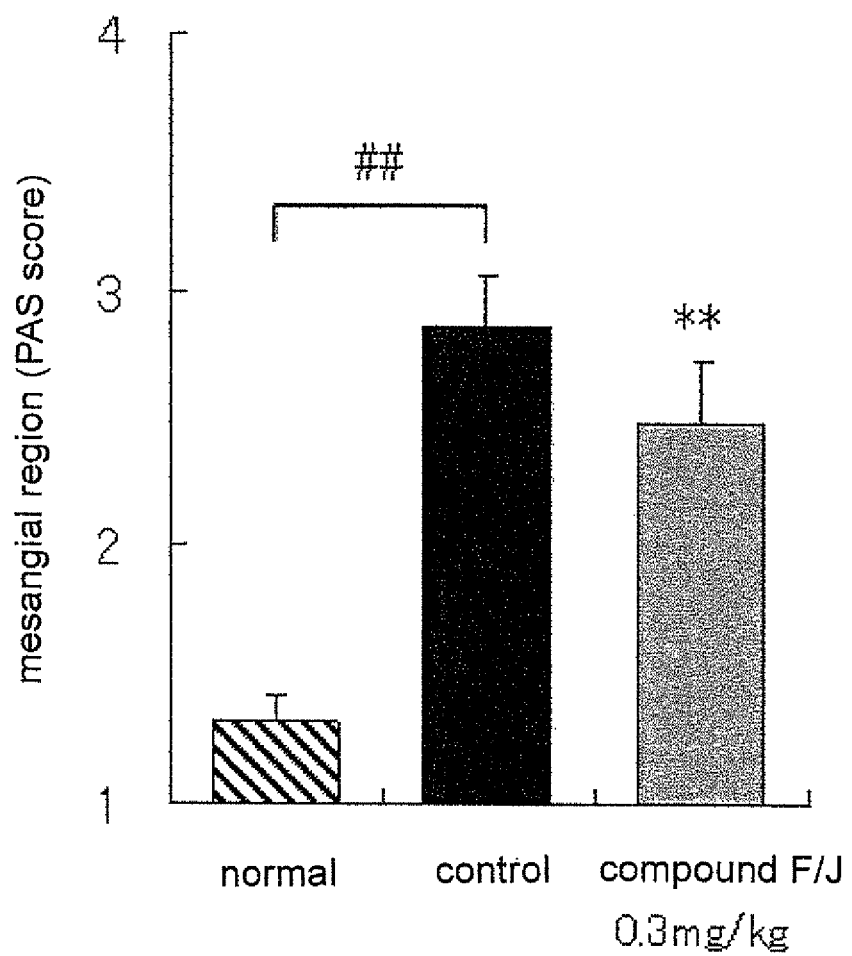
FIG. 9E shows the effect on renal histopathology (mesangial region) in rat anti Thy-1 antibody-induced glomerulonephritis model.
Figure 9F:
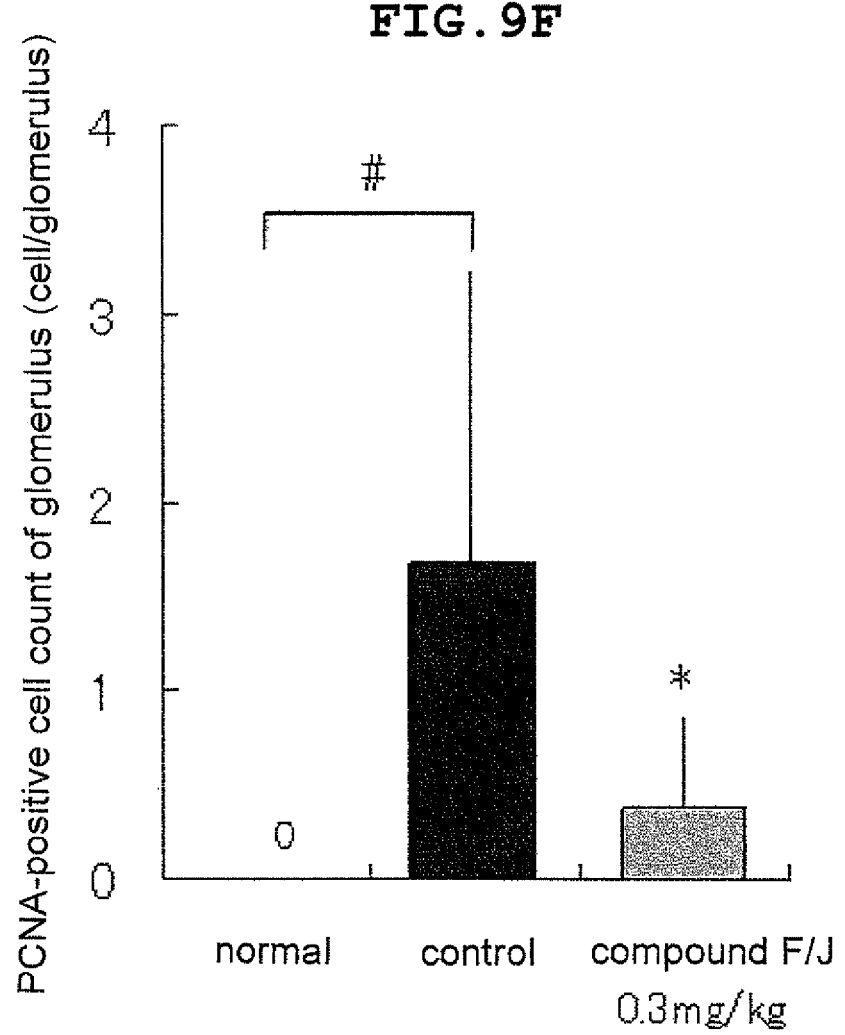
FIG. 9F shows the effect on renal histopathology (PCNA-positive glomerular cell count) in rat anti Thy-1 antibody-induced glomerulonephritis model.

As a result, body weight gain was suppressed in the control group as compared to the normal group after 1 day from the antibody administration. However, the body weight increased like the normal group after 3 days. The body weight of compound F/J-treated group showed a shift similar to that of the control group. The 24-hr urine volume of the control group increased as compared to the normal group. However, that of the compound F/J-treated group was of the same level as the normal group (FIG. 9A). The 24-hr urine protein markedly increased in the control group, whereas a lower value than control was found in the compound F/J-treated group (FIG. 9B). The relative kidney weight markedly increased in the control group, but a value lower than control and near the normal was observed in the compound F/J-treated group (FIG. 9C). Renal histopathological evaluation revealed that the control group remarkably increased the total glomerular cells, mesangial region and PCNA-positive cells in the glomerulus. The compound F/J-treated group significantly suppressed the increase in all of these measures (FIGS. 9D, 9E, 9F).

Therefore, the compound of the present invention normalizes the urine volume, decreases proteinuria and suppresses the immune reaction and growth reaction of glomerulus, indicating that it is effective for nephritis.

Example 31

Effect on Intraocular Pressure in Rabbits

Japanese white rabbits (male, 10 weeks old, BIOTEC Co., Ltd.) were purchased, acclimated for 1 week and used for the study. Compound F solution (0.01 w/v %) was instilled once into the cornea of both eyes at a volume of 50 µL/eye with a micropipette. The intraocular pressure of the right eye was measured and the local irritative effect on the eye was evaluated using the left eye. After surface anesthesia with oxybupranol (Benoxil 0.4% instillation solution), the intraocular pressure was measured before ocular instillation and 1, 2, 3, 4, 6 and 8 hr after the instillation using a pneumatonometer (Alcon Ltd.). In addition, the local irritative effect on the eye was evaluated by scoring conjunctival congestion, conjunctival edema, cornea opacity, iris congestion, excretion and eye closure performance. For the evaluation, phosphate buffer was used for the solvent control group, and isopropyl unoprostone (Rescula eye drops, Santen Pharmaceutical Co., Ltd.) was used for comparison. Six animals were used for each group and the results were expressed as average.

Figure 10:
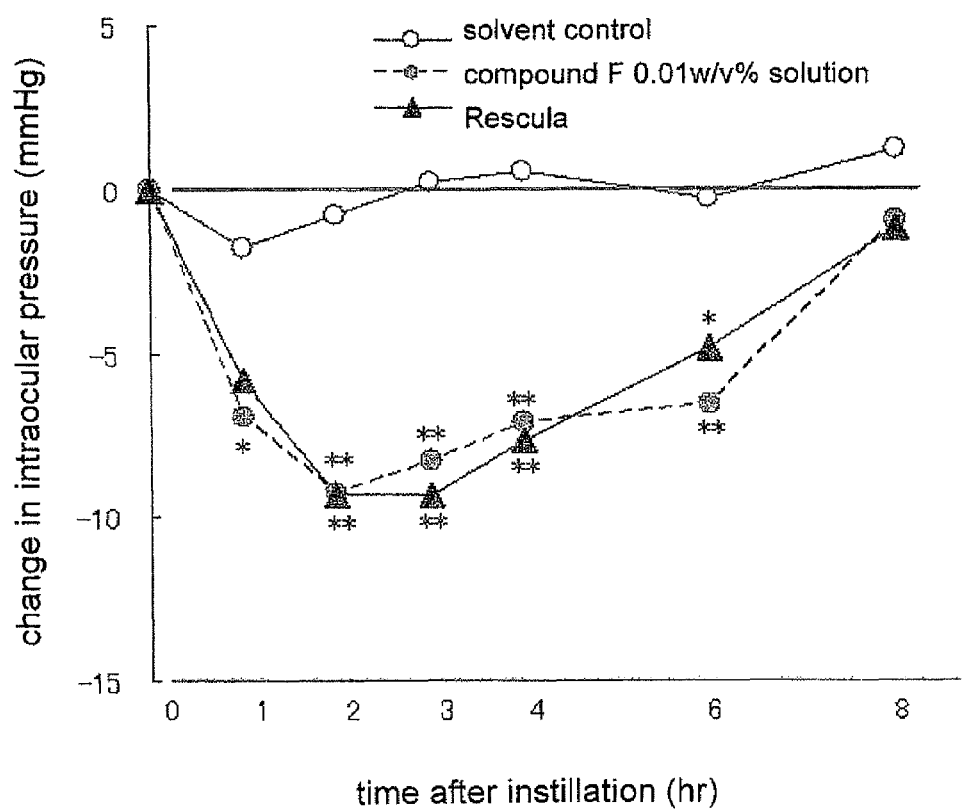
FIG. 10 shows the effect on rabbit intraocular pressure.

As a result, the intraocular pressure of the solvent control group shifted within the range of ±2 mmHg from the time 0 to 8 hrs after the instillation. The compound F group showed a decrease of 6.9 mmHg in intraocular pressure 1 hr after the instillation, of 9.3 mmHg 2 hr after, and of 6.6 mmHg 6 hr after, thus maintaining a significant decrease in the intraocular pressure. On the other hand, the Rescula eye drops group showed an intraocular pressure decrease profile mostly similar to that of the compound F group (FIG. 10).

As for the local irritant effect on the eye, conjunctival edema and eye closure were observed 1 hr after the instillation in some animals of the compound F group, but the animals recovered later. In the Rescula eye drops group, conjunctival edema and eye closure in some animals were observed 1 hr after the instillation and lasted for up to 2 hr after the administration. The animals recovered later.

Therefore, the compound F of the present invention shows an intraocular pressure lowering effect and a local irritant effect on the eye equivalent to those of Rescula eye drops, and is useful as a therapeutic agent for glaucoma and high intraocular pressure.

Example 32

Prophylactic Effect on Concanavalin A-Induced Hepatitis Model in Mice

The prophylactic effect of compound F on hepatitis was investigated using concanavalin A (hereinafter Con A)-induced hepatitis model. This model is a hepatitis model in which parenchymal hepatocytes are injured in a T cell-dependent manner, and exhibits similar clinical pathology to autoimmune hepatitis or fulminant hepatitis (see: References N, O, and P).

BALB/c mice (female, 7 weeks old, Japan SLC) were purchased, acclimated for 1 week and used for the study. Except the no-induction group, Con A (type IV, Sigma-Aldrich) dissolved in saline was administered from the tail vein of the mice at a dose of 12.5 mg/10 mL/kg to induce hepatitis. Twenty hr later, the mice were subjected to laparotomy under ether anesthesia. A 0.5 mL of blood sample was collected from the caudal vena cava and heparinized plasma was obtained to measure plasma ALT and AST activities. Test substances were compound F (1 mg/10 mL solution), prednisolone (Nacalai Tesque, 5 mg/10 mL suspension (with 0.5 w/v % methylcellulose)) and water for injection (administered to the control group), which were orally administered at a volume of 10 mL/kg 1 hr before Con A injection. Seven to 9 animals were used for each group. After logarithmic transformation of the data, one-way analysis of variance was performed for statistical evaluation.

Figure 11:
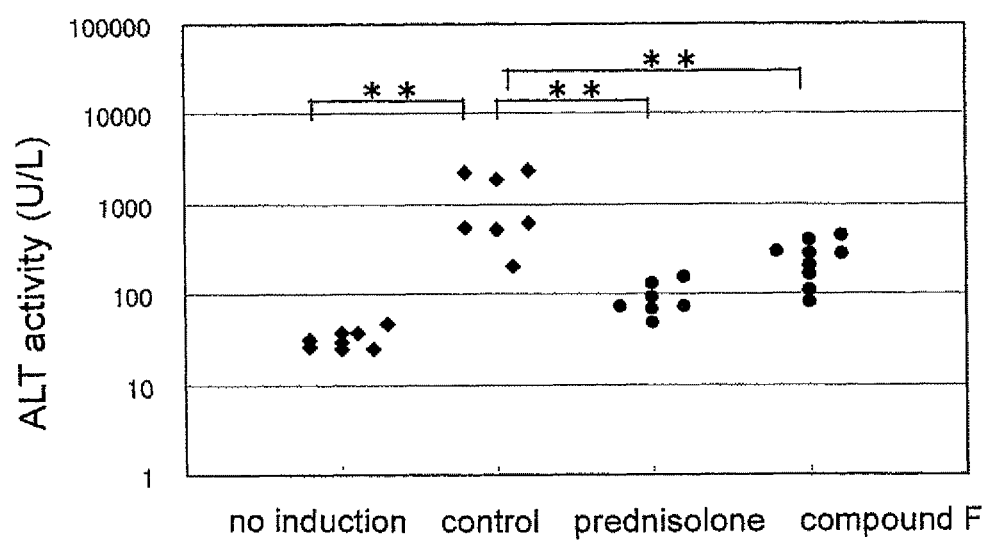
FIG. 11 shows the prophylactic effect in mouse concanavalin A-induced hepatitis model.

As a result, plasma ALT and plasma AST activities of the control group remarkably increased as compared to those of the no-induction group. Compound F and prednisolone significantly and strongly suppressed the increase. FIG. 11 shows the data of plasma ALT.

Therefore, compound F is effective for T cell activation associated hepatic injury.

REFERENCES

N) Eur. J. Immunol. 28(12): 4105-4113 (1998).
O) Proc. Natl. Acad. Sci. 97(10): 5498-5503 (2000).
P) J. Exp. Med. 191(1): 105-114 (2000).

INDUSTRIAL APPLICABILITY

Compound (1) of the present invention is useful as an active ingredient of medicaments. A medicament containing compound (1) of the present invention as an active ingredient is useful for immune diseases, diseases of the digestive tract, cardiovascular diseases, cardiac diseases, respiratory diseases, neurological diseases, ophthalmic diseases, renal diseases, hepatic diseases, bone diseases, skin diseases and the like, each involving EP4. Particularly, it is useful as a medicament for the prophylaxis or treatment of ulcerative colitis, Crohn's disease, gastritis or gastric ulcer, small intestinal ulcer, nephritis, glaucoma or hepatitis.

The invention claimed is:

1. A method of treating osteoporosis in a subject, comprising administrating an effective amount of a compound of formula (1):

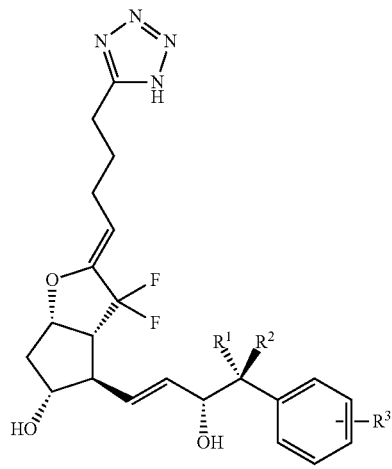

wherein $R^1$ and $R^2$ are each independently a hydrogen atom or a straight chain alkyl group having a carbon number of 1 to 3, and $R^3$ is a hydrogen atom, an alkyl group having a carbon number of 1 to 4, an alkoxyalkyl group, an aryl group, a halogen atom, or a haloalkyl group, or a pharmaceutically acceptable salt thereof, as an active ingredient to a subject with osteoporosis, thereby treating osteoporosis in the subject.

2. A method of treating a bone fracture in a subject, comprising administrating an effective amount of a compound of formula (1):

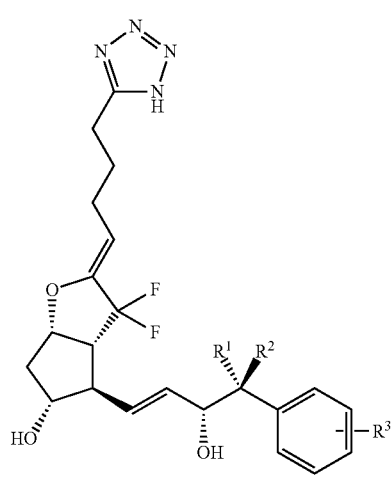

wherein $R^1$ and $R^2$ are each independently a hydrogen atom or a straight chain alkyl group having a carbon number of 1 to 3, and $R^3$ is a hydrogen atom, an alkyl group having a carbon number of 1 to 4, an alkoxyalkyl group, an aryl group, a halogen atom, or a haloalkyl group, or a pharmaceutically acceptable salt thereof, as an active ingredient to a subject with a bone fracture, thereby treating the bone fracture in the subject.

3. A method of treating neuronal cell death in a subject, comprising administrating an effective amount of a compound of formula (1):

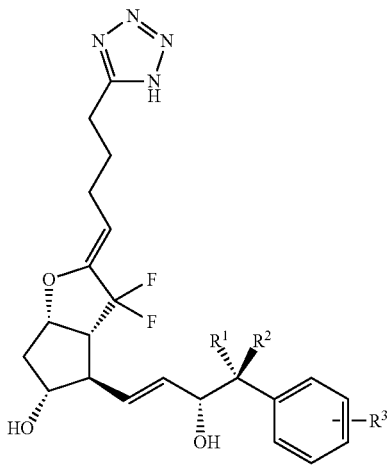

(1)

wherein $R^1$ and $R^2$ are each independently a hydrogen atom or a straight chain alkyl group having a carbon number of 1 to 3, and $R^3$ is a hydrogen atom, an alkyl group having a carbon number of 1 to 4, an alkoxyalkyl group, an aryl group, a halogen atom, or a haloalkyl group, or a pharmaceutically acceptable salt thereof, as an active ingredient to a subject with neuronal cell death, thereby treating neuronal cell death in the subject.

4. A method of treating amyotrophic lateral sclerosis in a subject, comprising administrating an effective amount of a compound of formula (1):

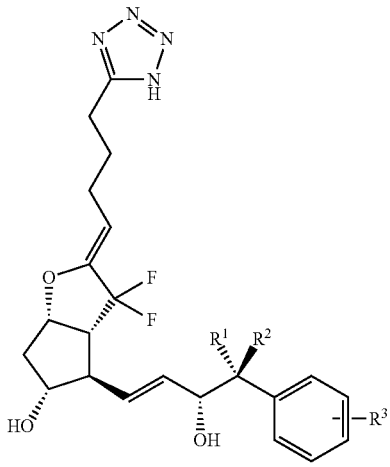

(1)

wherein $R^1$ and $R^2$ are each independently a hydrogen atom or a straight chain alkyl group having a carbon number of 1 to 3, and $R^3$ is a hydrogen atom, an alkyl group having a carbon number of 1 to 4, an alkoxyalkyl group, an aryl group, a halogen atom, or a haloalkyl group, or a pharmaceutically acceptable salt thereof, as an active ingredient to a subject with amyotrophic lateral sclerosis, thereby treating amyotrophic lateral sclerosis in the subject.

5. A method of treating multiple sclerosis in a subject, comprising administrating an effective amount of a compound of formula (1):

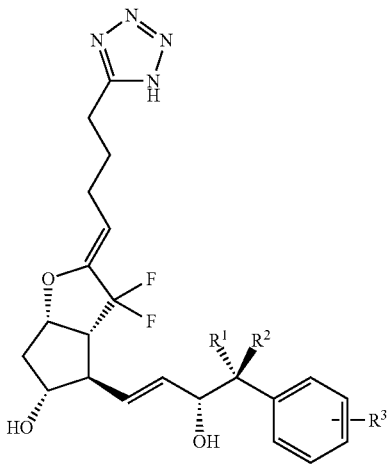

(1)

wherein $R^1$ and $R^2$ are each independently a hydrogen atom or a straight chain alkyl group having a carbon number of 1 to 3, and $R^3$ is a hydrogen atom, an alkyl group having a carbon number of 1 to 4 an alkoxyalkyl group, an aryl group, a halogen atom, or a haloalkyl group, or a pharmaceutically acceptable salt thereof, as an active ingredient to a subject with multiple sclerosis, thereby treating multiple sclerosis in the subject.

* * * * *